United States Patent [19]

Hagiwara et al.

[11] Patent Number: 5,472,823
[45] Date of Patent: Dec. 5, 1995

[54] PHOTOSENSITIVE RESIN COMPOSITION

[75] Inventors: Hideo Hagiwara; Makoto Kaji, both of Hitachi; Hiroshi Nishizawa, Kitaibaraki; Kenji Suzuki; Yasunori Kojima, both of Hitachi, all of Japan

[73] Assignee: Hitachi Chemical Co., Ltd., Tokyo, Japan

[21] Appl. No.: 5,210

[22] Filed: Jan. 15, 1993

[30] Foreign Application Priority Data

Jan. 20, 1992 [JP] Japan .................. 4-007467
Nov. 9, 1992 [JP] Japan .................. 4-298560

[51] Int. Cl.⁶ .............. G03C 1/68; C08G 73/10
[52] U.S. Cl. .............. 430/270; 430/195; 430/196; 430/283; 430/296; 528/26; 528/170; 528/171; 528/172; 528/173; 528/174; 528/179; 528/183; 528/185; 528/220; 528/229; 528/335; 528/336; 528/341; 528/342; 528/345; 528/351; 528/353
[58] Field of Search ............ 528/183, 185, 528/353, 179, 26, 170–174, 336, 220, 229, 335, 341, 345, 342, 351; 430/270, 195, 196, 283, 296

[56] References Cited

U.S. PATENT DOCUMENTS

| | | | |
|---|---|---|---|
| 4,310,641 | 1/1982 | Ohmura et al. | 525/419 |
| 4,311,785 | 1/1982 | Ahne et al. | 430/283 |
| 4,321,319 | 3/1982 | Shoji et al. | 430/270 |
| 4,356,247 | 10/1982 | Aotani et al. | 430/195 |
| 4,451,551 | 5/1984 | Kataoka et al. | 430/270 |
| 4,565,767 | 1/1986 | Kataoka et al. | 430/196 |
| 4,645,823 | 2/1987 | Ai et al. | 528/336 |
| 4,656,244 | 4/1987 | Ahne | 528/336 |
| 4,801,681 | 1/1989 | Ahne | 528/336 |

*Primary Examiner*—P. Hampton-Hightower
*Attorney, Agent, or Firm*—Antonelli, Terry, Stout & Kraus

[57] ABSTRACT

A photosensitive resin composition comprising, as its main ingredient, a poly(amic acid) resin constituted of a diamino compound represented by formula:

$$\underset{H_2N-R_1-NH_2}{(NHCONH-X)_p} \quad (I)$$

and optionally used other diamino compound and a tetra-carboxylic acid dianhydride as its constituent monomers and/or a poly(amic acid) ester resin obtained by esterifying said poly(amic acid) resin and/or a polyimide resin obtained by a dehydrating or alcohol-eliminating ring-closure reaction of said poly(amic acid) resin or poly(amic acid) ester resin has an excellent developability and a high film strength and can form a relief patter of low thermal expansion.

5 Claims, 6 Drawing Sheets

PHOTOSENSITIVE RESIN COMPOSITION

BACKGROUND OF THE INVENTION

This invention relates to a diamino compound, a poly(amic acid) resin, a poly(amic acid) ester resin, a polyimide resin, processes for producing them, photosensitive resin compositions containing said resins, and polyimidazopyrrolone resins or polyimidazopyrroloneimide resins obtained from said resins or from photosensitive resin compositions containing said resins.

In the current semiconductor industry, the inorganic materials having hitherto been used as an interlaminar insulating material are being replaced by organic materials excellent in heat resistance and particularly by polyimide resin and the like because of their excellent properties.

Since the formation of a circuit pattern on a semiconductor integrated circuit or a printed circuit involves complicated and divergent procedures such as resist film formation on the substrate surface, exposure of necessary areas to light, removal of unnecessary areas by etching or the like, cleaning of the substrate surface, etc., it is waited for to develop a heat-resistant photosensitive material which makes it possible to leave the resist material of necessary parts as it is in order to use it as an insulating material even after patterns have been formed by exposure and development.

As such materials, heat-resistant photosensitive materials using a photosensitive polyimide, a cyclized polybutadiene or the like as a mainly used polymer have been proposed. Among them, photosensitive polyimide is-noticed with a particular interest because it is excellent in heat resistance and the removal of impurities therefrom is easy to practice. As one example of such photosensitive polyimide, Japanese Patent Examined Publication No. 55-30207 proposed a photosensitive polyimide precursor prepared by introducing a photosensitive group into a polyimide precursor through an ester bonding. However, this material is disadvantageous in that, since an acid chloride is used in the synthesis of the photosensitive polyimide precursor, the finally obtained photosensitive resin composition is readily contaminated by chloride. Further, this resin is difficult to make into a material of high molecular weight, so that it is inferior in film strength.

As another example, Japanese Patent Unexamined Publication No. 57-168942 proposed a photosensitive composition comprising a mixture of a poly(amic acid) and an amine having photo-crosslinkable functional group as its main ingredient. However, this photosensitive composition is disadvantageous in that the bonding force between poly(amic acid) and the photosensitive functional group is relatively weak and therefore this composition is low in the development latitude.

In Japanese Patent Unexamined Publication No. 54-95697, there is proposed a photosensitive composition comprising a mixture of poly(amic acid) and a polymerizable unsaturated compound having acryl functional group or the like as its main ingredient. However, this composition is narrow in its development latitude due to a small difference between the solubility of non-exposed areas to a developer and that of exposed areas to the developer. The term "development latitude" means a time between the minimum time necessary for removing non-exposed areas by development and the maximum time not corroding exposed areas by development. The larger the development latitude, the better the workability.

SUMMARY OF THE INVENTION

It is an object of this invention to solve the above-mentioned problems of the prior art by providing a photosensitive resin composition capable of forming a relief pattern excellent particularly in developability and simultaneously having a high film strength, a high heat resistance and a high adhesive property, a poly(amic acid) resin, a poly(amic acid) ester resin and a polyimide resin useful for preparing said composition, a novel diamino compound useful as a constituent monomer of these resins, and a polyimidazopyrrolone resin or polyimidazopyrroloneimide resin suitable for use as said relief pattern.

This invention provides a diamino compound represented by the formula:

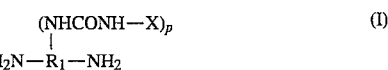

wherein X is a monovalent photosensitive group; $R_1$ is a (2+p)-valent organic group; and p is an integer of 1 to 12.

This invention further provides a process for producing a diamino compound of formula (I), which comprises adding an isocyanate compound having one or more vinyl groups to a polyamino compound.

This invention further provides a poly(amic acid) resin having recurring units represented by the formula:

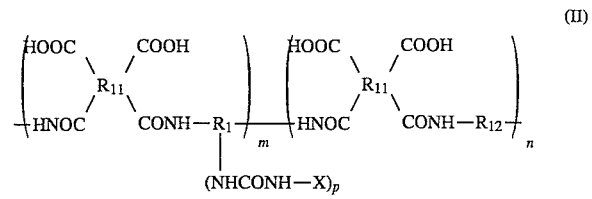

wherein X is a monovalent photosensitive group; $R_1$ is (2+p)-valent organic group; $R_{11}$ is a tetravalent organic group; $R_{12}$ is a divalent organic group; p is an integer of 1 to 12; and m and n are molar numbers of the recurring units, and m/n is 1/99 to 100/0 as expressed in terms of molar ratio.

This invention further provides a poly(amic acid) ester resin wherein the carboxyl group in the poly(amic acid) resin is esterified with a compound having no vinyl group, and a polyimide resin obtained by subjecting said poly(amic acid) resin or its corresponding poly(amic acid) ester resin to a dehydrating or alcohol-eliminating ring-closure.

This invention further provides a process for producing the poly(amic acid) resin of formula (II), which comprises reacting a diamino compound including the novel diamino compound of formula (I) with a tetracarboxylic acid dianhydride in an organic solvent.

This invention further provides a photosensitive resin composition comprising:

(A) a poly(amic acid) resin having recurring units of formula (II), a poly(amic acid) ester resin prepared by esterifying its carboxyl group and/or a polyimide resin prepared by subjecting them to a dehydrating or alcohol-eliminating ring-closure, and (B) a photoinitiator as an optional ingredient.

This invention further provides a polyimidazopyrrolone resin or a polyimidazopyrroloneimide resin obtained by a ring-closure reaction at an elevated temperature of poly(amic acid) having recurring units of formula (II), a poly(amic acid) ester resin prepared by esterifying its carboxyl group and/or a polyimide resin prepared by dehydrating or alcohol-eliminating ring-closure of them or a photosensitive resin composition comprising these resins.

As used herein, the term "polyimidazopyrroloneimide resin" means a polymer having an imidazopyrrolone ring structure and an imide ring structure. When p=2 and n=0 in formula (II), a polyimidazopyrrolone resin is obtained. When p=2 and n>0 or when p=1 in formula (II), a polyimidazopyrroloneimide resin is obtained.

DESCRIPTION OF THE PREFERRED EMBODIMENTS

Figure 1:
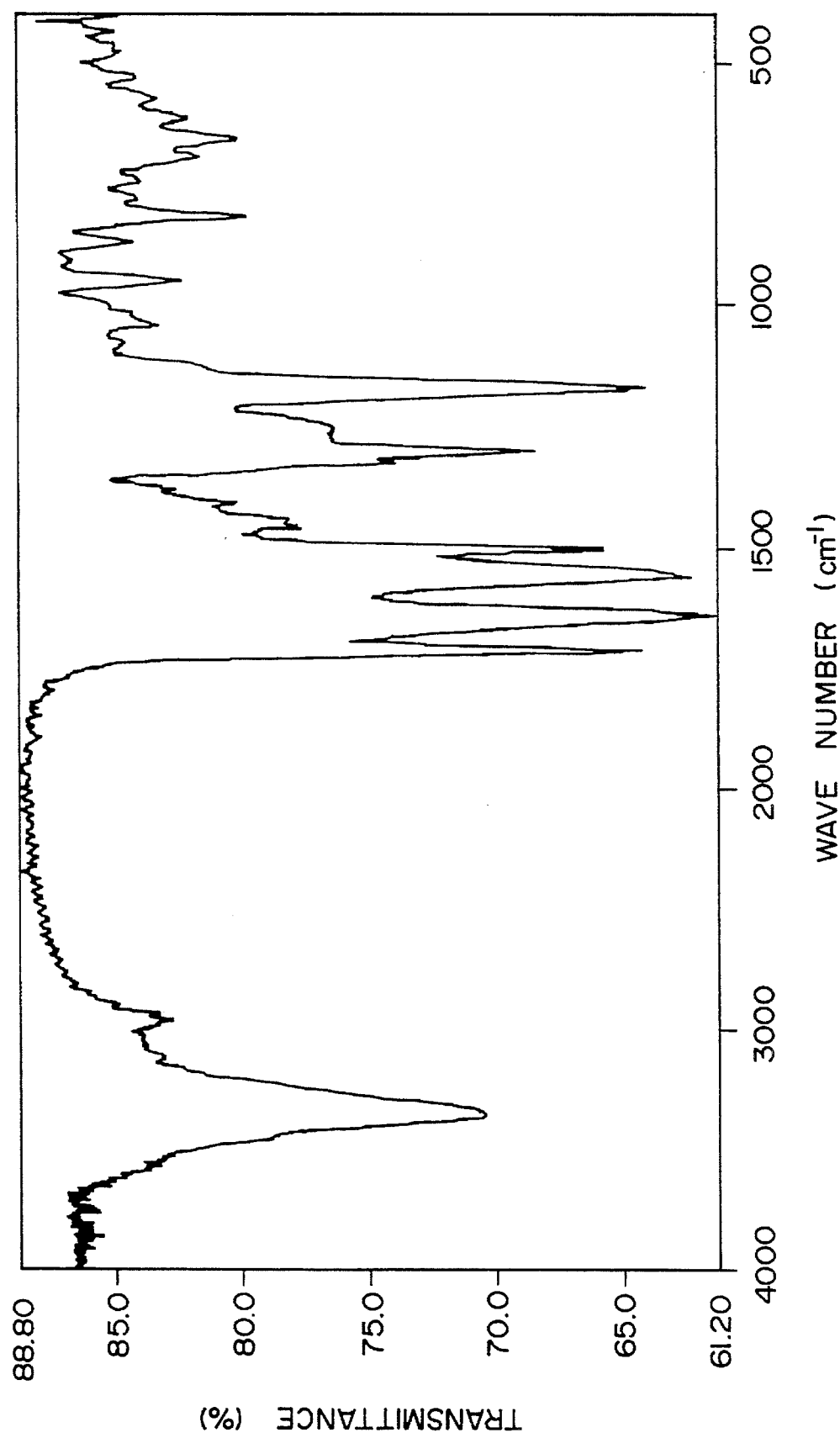
FIG. 1 is an IR spectrum of the product obtained in Synthesis Example 1.

The diamino compound of this invention is represented by the formula:

(I)

wherein X is a monovalent photosensitive group; and $R_1$ is a (2+p)-valent organic group; and p is an integer of 1 to 12. When p=1, the one —(NHCONH—X) group and one of the two amino groups are separately linked to two adjacent atoms in $R_1$, respectively. When p=2, the two —(NHCONH—X) groups are separately linked to two separate atoms in $R_1$ adjacent to two separate atoms to which the two amino groups are linked, respectively. When p is 3 or more, each —(NHCONH—X) group is linked to each atom in $R_1$.

In the formula (I), X represents a monovalent photosensitive group. As used herein, the term "photosensitive group" means an organic group having a group polymerizable, dimerizable or crosslinkable by the action of light. As such a photosensitive group, hitherto known photosensitive groups can be used without limitation. From the viewpoint of sensitivity, however, organic groups having a vinyl group are preferable.

Such preferable organic groups are shown below in terms of formula (III):

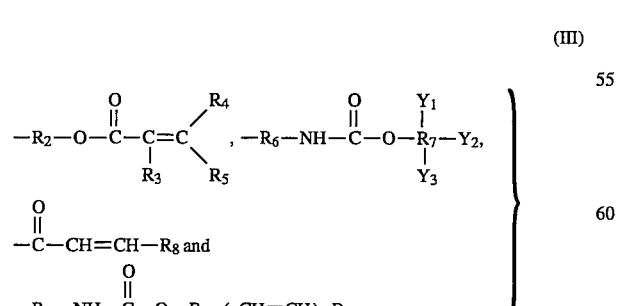
(III)

wherein $R_2$ is a divalent group derived from an alkyl group; $R_6$ and $R_9$ are independently a divalent group derived from an alkyl group, a divalent group derived from a cycloalkyl group optionally having a methyl or methoxy group or a divalent aromatic group optionally having a methyl or methoxy group; $R_{10}$ is a divalent organic group; $R_3$, $R_4$ and $R_5$ are independently a hydrogen atom or an alkyl group; $R_7$ is a tetravalent organic group; $R_8$ is a monovalent aromatic group or a heterocyclic group; $Y_1$, $Y_2$ and $Y_3$ are independently a hydrogen atom or a monovalent organic group having a vinyl group, provided that at least one of $Y_1$, $Y_2$ and $Y_3$ is a monovalent organic group having a vinyl group; and k is 1 or 2.

Herein, the divalent group derived from an alkyl group represented by $R_2$ is not particularly limited. However, it has preferably 1–18 carbon atoms, more preferably 1–5 carbon atoms, and particularly preferably 2–4 carbon atoms. If the number of the carbon atoms is too large, the vaporization loss at the time of hot cure is great and the resolution tends to be deteriorated.

Although the alkyl group represented by $R_3$, $R_4$ and $R_5$ is not particularly limited, it has preferably 1–3 carbon atoms.

Preferable examples of the divalent group derived from an alkyl group, a divalent group derived from a cycloalkyl group optionally having a methyl or methoxy group and a divalent aromatic group optionally having a methyl or methoxy group represented by $R_6$ and $R_9$ include the following:

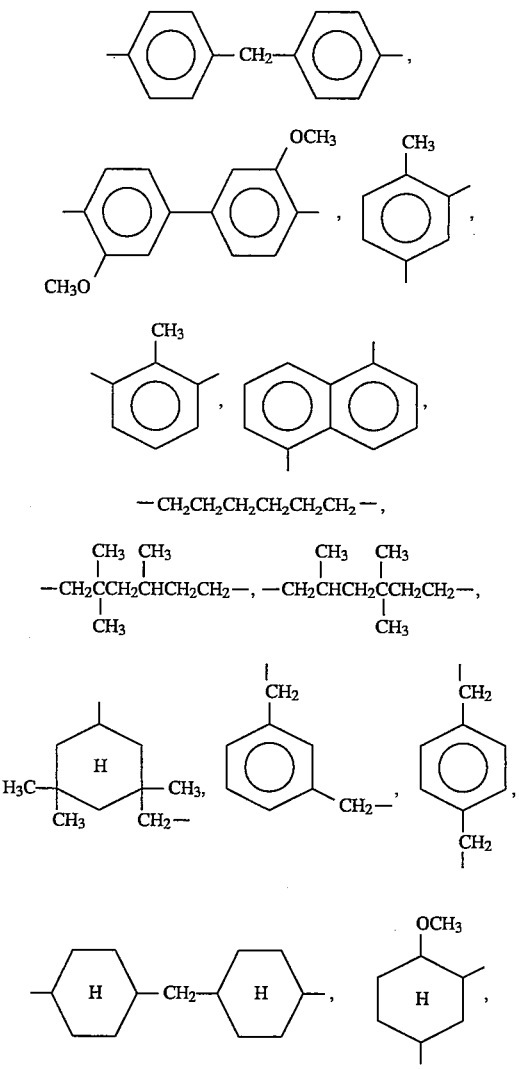

-continued

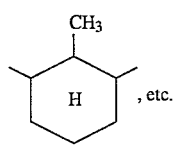, etc.

The tetravalent organic group represented by $R_7$ is preferably a tetravalent group derived from an alkyl group or one of the following groups:

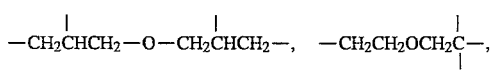

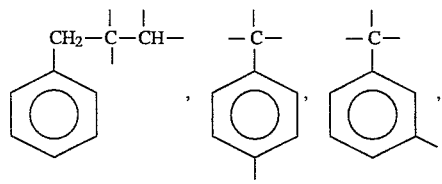

-continued

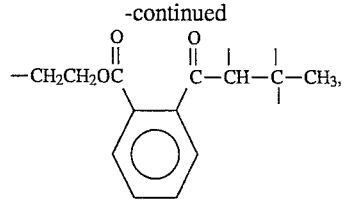

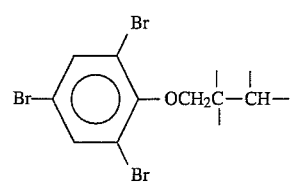

Said tetravalent group derived from an alkyl group preferably has 1–10 carbon atoms, and more preferably 1–6 carbon atoms.

In the formula (I), $R_1$ is a (2+p)-valent organic group wherein p is 1 to 12, namely a trivalent, tetravalent or higher valent organic group. As examples of the organic group, the following ones can be referred to:

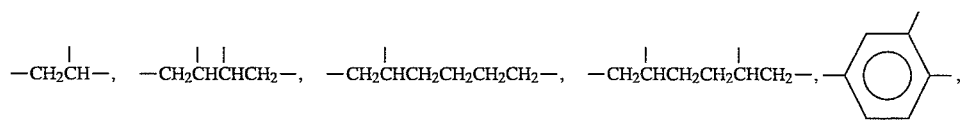

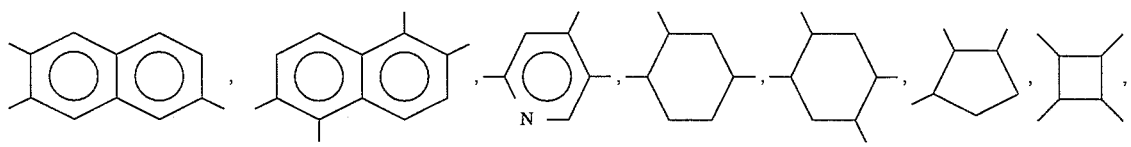

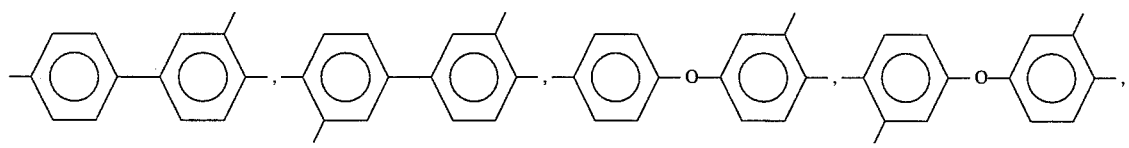

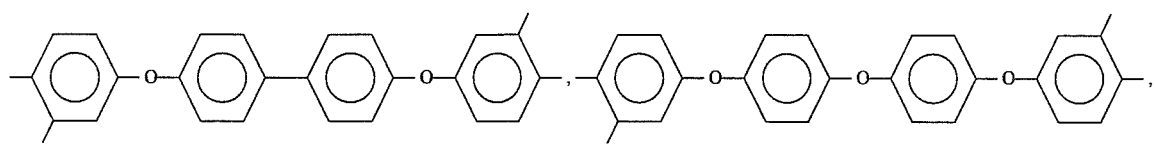

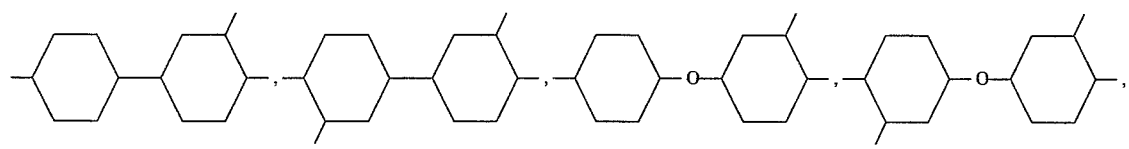

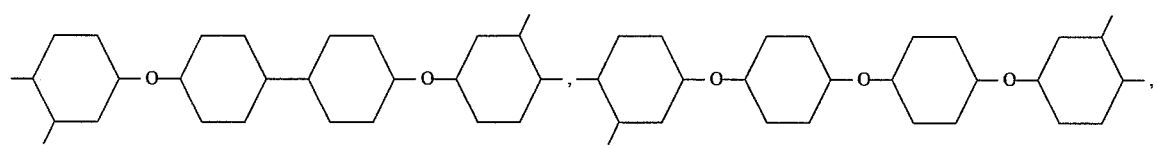

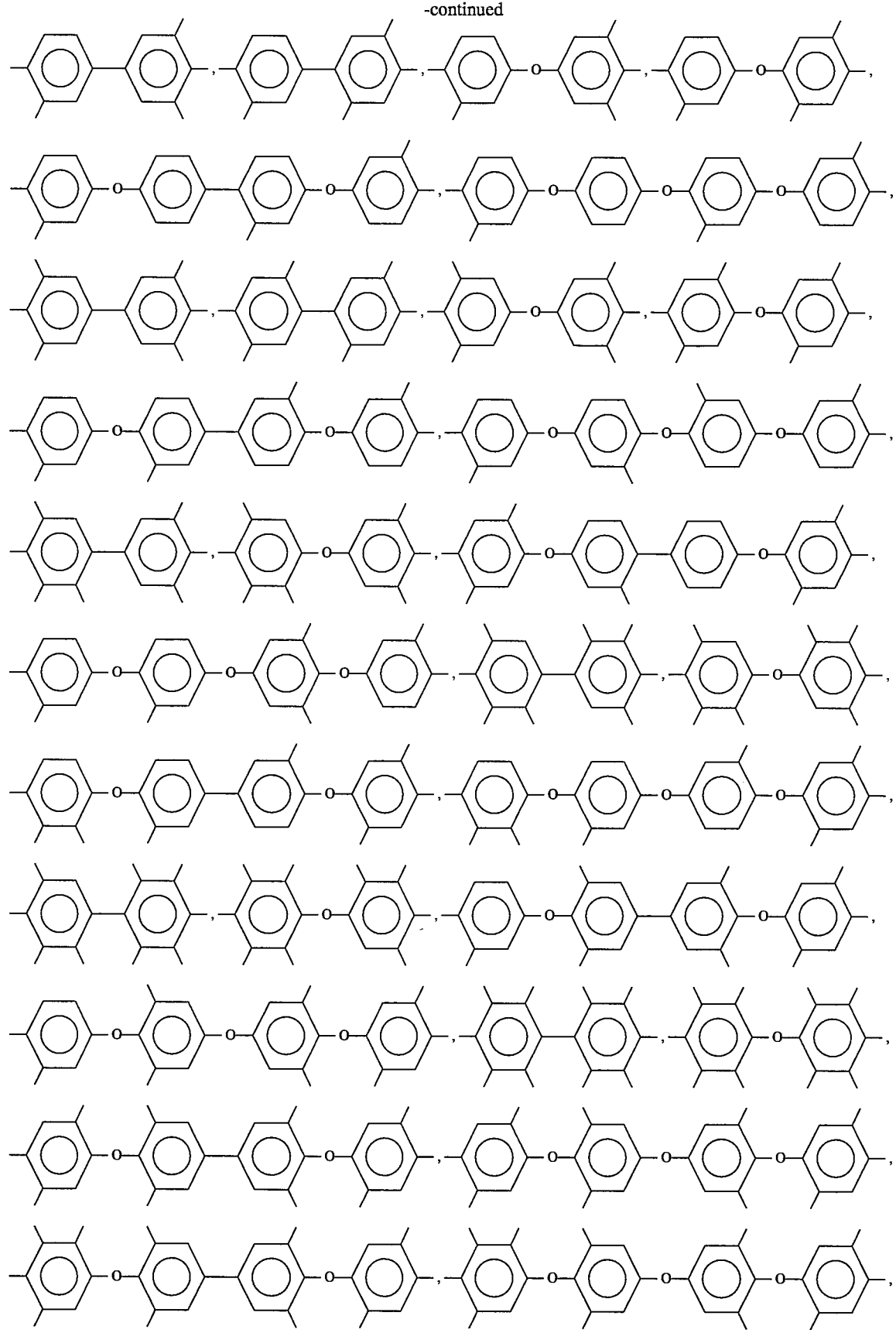

-continued

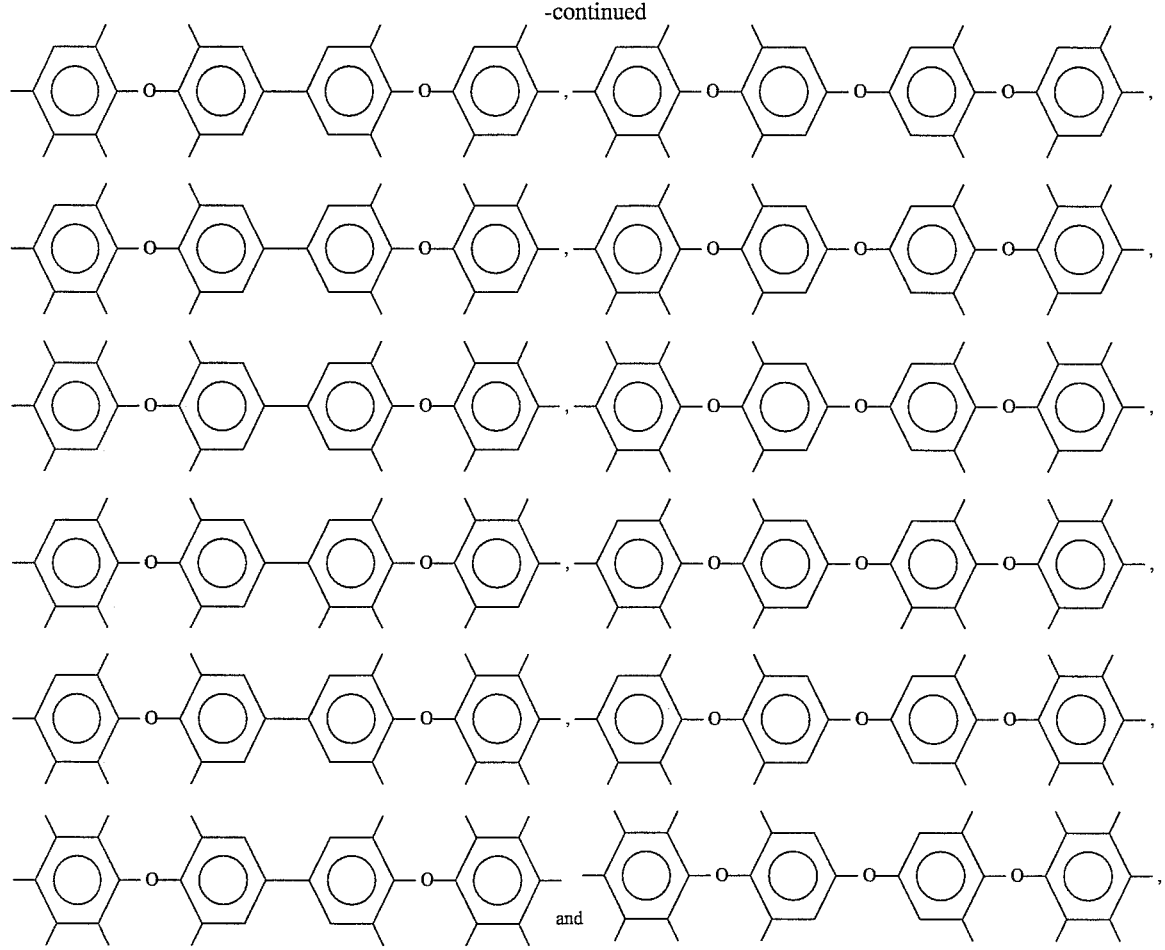

Among these groups, the following groups are preferable:

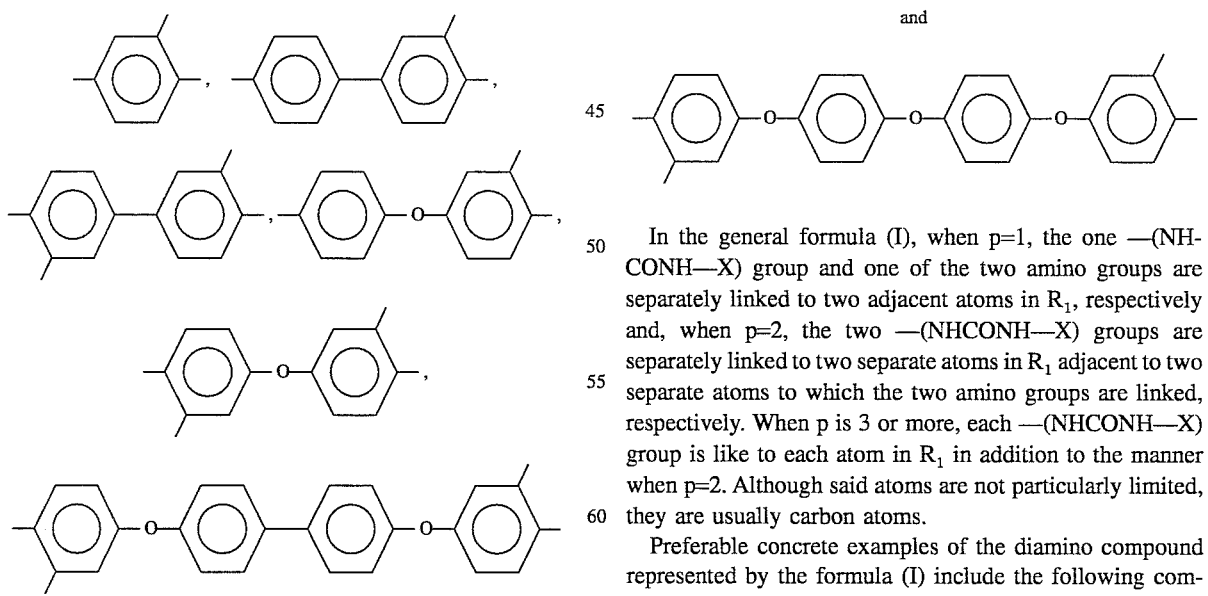

and

In the general formula (I), when p=1, the one —(NH-CONH—X) group and one of the two amino groups are separately linked to two adjacent atoms in $R_1$, respectively and, when p=2, the two —(NHCONH—X) groups are separately linked to two separate atoms in $R_1$ adjacent to two separate atoms to which the two amino groups are linked, respectively. When p is 3 or more, each —(NHCONH—X) group is like to each atom in $R_1$ in addition to the manner when p=2. Although said atoms are not particularly limited, they are usually carbon atoms.

Preferable concrete examples of the diamino compound represented by the formula (I) include the following compounds:

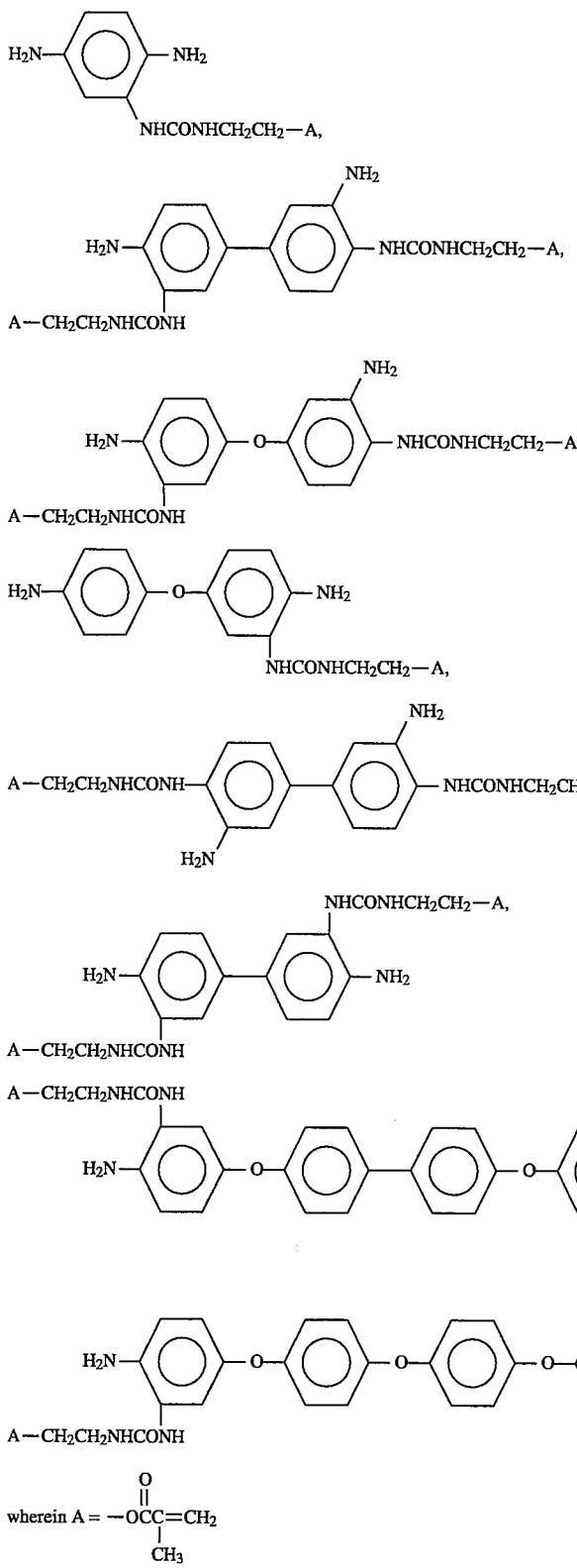

wherein A = $-\text{O}\overset{\text{O}}{\overset{\|}{\text{C}}}\text{C}=\text{CH}_2$
$\qquad\qquad\quad\;\;|$
$\qquad\qquad\;\;\,\text{CH}_3$ The diamino compound represented by the formula (I) can be produced, for example, by adding an isocyanate compound having a vinyl group to a polyamino compound in an organic solvent. Apart from this method, various known methods can be applied to the synthesis of the diamino compound of the formula (I).

As said polyamino compound, aromatic polyamino compounds including triamines and tetraamines such as 1,2,3-triaminobenzene, 1,2,4-triaminobenzene, 1,2,4,5-tetraaminobenzene, 3-aminobenzidine, 3,3'-diaminobenzidine, 3,4,4'-triaminodiphenyl ether, 3,3',4,4'-tetraaminodiphenyl ether, 3,4,4'-triaminobenzophenone, 3,3',4,4'-tetraaminobenzophenone, 3,4,4'-triaminodiphenylmethane, 3,3',4,4'-tetraaminodiphenylmethane, 3,4,4'-triaminodiphenyl sulfide, 3,3',4,4'-tetraaminodiphenyl sulfide, 3,4,4'-triaminodiphenyl sulfone, 3,3',4,4'-tetraaminodiphenyl sulfone, 2,2-bis(3,4-diaminophenyl)-propane, 4,4'-bis(3,4-diaminophenoxy)biphenyl, 2,2-bis[4-(3,4-diaminophenoxy)phenyl]-propane, 2,2-bis(3,4-diaminophenyl)-hexafluoropropane, 2,2-bis[4-(3,4-diaminophenoxy)phenyl]-hexafluoropropane and the like, the compounds having the following structural formulas, and the like, as well as alicyclic polyamino compounds prepared by hydrogenating said aromatic polyamino compounds, are preferable.

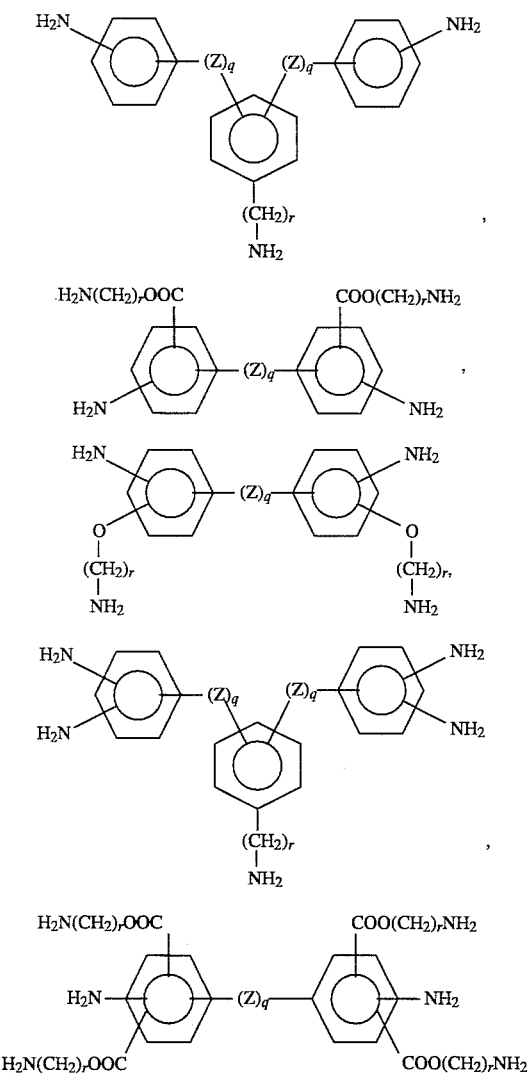

wherein Z is oxygen atom or sulfur atom; q is 0 or 1; and r is 1–5.

These amino compounds may be used either singly or in combination of two or more members. The following diamino compounds are preferably usable in this invention:

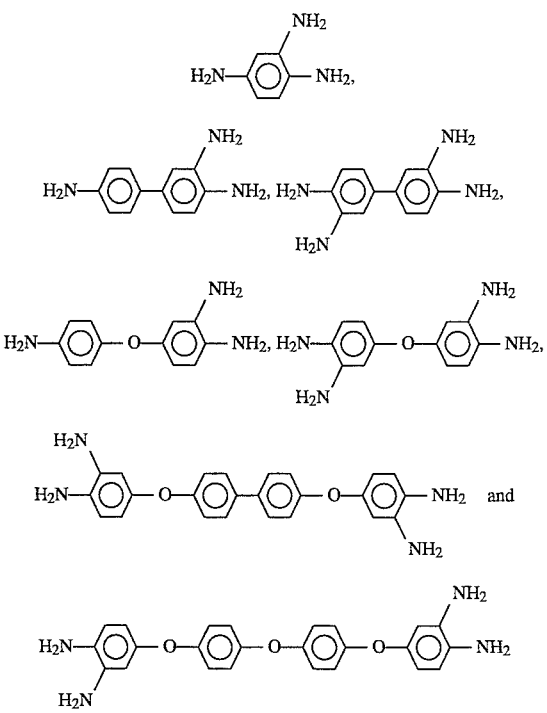

As the isocyanate compound having vinyl group, the compounds represented by the following formulas (IV) and (V) are preferably used:

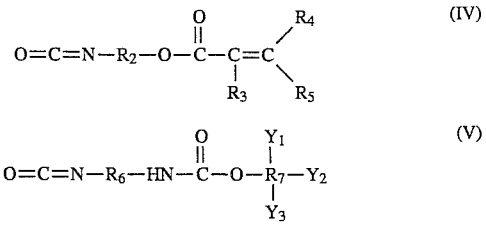

wherein $R_2$, $R_6$, $R_3$, $R_4$, $R_5$, $R_7$, $Y_1$, $Y_2$ and $Y_3$ are as defined in formula (III).

Examples of the isocyanate compound represented by formula (IV) include isocyanatoethyl acrylate, isocyanatopropyl acrylate, isocyanatobutyl acrylate, isocyanatopentyl acrylate, isocyanatohexyl acrylate, isocyanatooctyl acrylate, isocyanatodecyl acrylate, isocyanatooctadecyl acrylate, isocyanatoethyl methacrylate, isocyanatopropyl methacrylate, isocyanatobutyl methacrylate, isocyanatopentyl methacrylate, isocyanatohexyl methacrylate, isocyanatooctyl methacrylate, isocyanatodecyl methacrylate, isocyanatooctadecyl methacrylate, isocyanatoethyl crotonate, isocyanatopropyl crotonate, isocyanatohexyl crotonate and the like, among which isocyanatoethyl methacrylate is preferable.

The isocyanate compound represented by formula (V) is synthesized from a hydroxy compound having at least one ethylenic unsaturated group and a polyisocyanate compound. Examples of said hydroxy compound having at least one ethylenic unsaturated group include trimethylolpropane diacrylate, trimethylolpropane dimethacrylate, trimethylolethane diacrylate, trimethylolethane dimethacrylate, pentaerythritol triacrylate, pentaerythritol trimethacrylate, 2-hydroxyethyl acrylate, 2-hydroxyethyl methacrylate, 2-hydroxypropyl acrylate, 2-hydroxypropyl methacrylate, 2-hydroxy-3-phenoxypropyl acrylate, 2-hydroxy-3-phenoxypropyl methacrylate, allyl alcohol, glycerin diallyl ether, trimethylpropane diallyl ether, trimethylolethane diallyl ether, pentaerythritol diallyl ether, ethyleneglycol monoallyl ether, diethyleneglycol monoallyl ether, diglycerol triallyl ether, crotyl alcohol, vinylphenol, cinnamyl alcohol, allylphenol, o-cinnamylphenol and the compounds of the formulas shown below. These hydroxy compounds may be used either singly or in combination of two or more members.

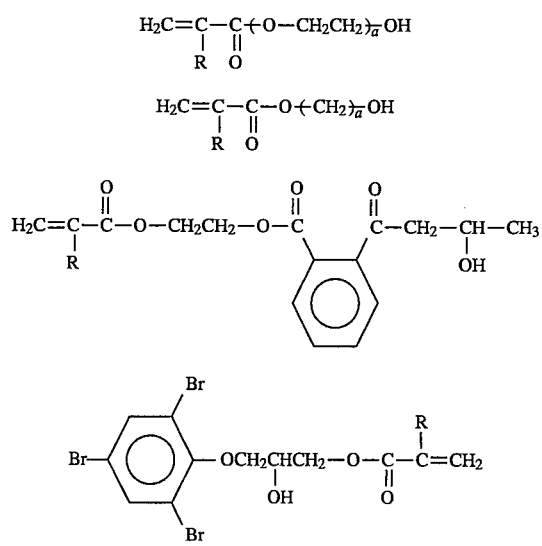

wherein a is an integer of 2–30 and R is hydrogen or methyl group.

Examples of the diisocyanate compound which reacts with the above-mentioned hydroxy compound to give a monoisocyanate compound having a carbon-carbon double bond and a urethane bond in its molecule include 4,4'-diphenylmethane diisocyanate, dianisidine diisocyanate, tolylene diisocyanate, hexamethylene diisocyanate, 2,4-tolylene diisocyanate, 2,6-tolylene diisocyanate, 1,5-naphthalene diisocyanate, trans-vinylene diisocyanate, 2,2,4-trimethylhexamethylene diisocyanate, 2,4,4-trimethylhexamethylene diisocyanate, 3-isocyanatomethyl-3,5,5-trimethyl-cyclohexyl isocyanate and the compounds represented by the formulas shown below. These compounds may be used either singly or in combination of two or more members.

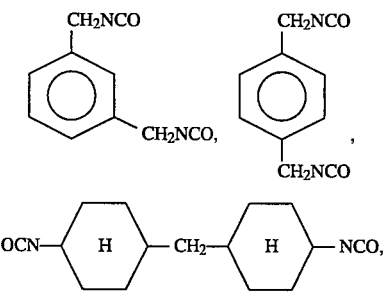

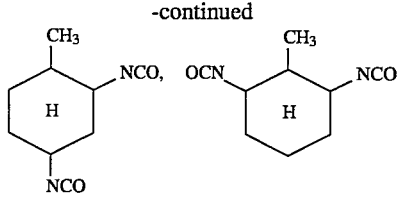

The reaction between the hydroxy compound having at least one ethylenic unsaturated group in the molecule and the diisocyanate is carried out in the absence or presence of an inert organic solvent usually at a temperature of 0°–100° C., preferably 20°–70° C. The ratio between the two compounds is preferably 0.8/1 to 1.2/1 and particularly preferably 1/1, as expressed in terms of molar ratio of the former to the latter.

The reaction between the hydroxy compound having at least one ethylenic unsaturated group in the molecule and the diisocyanate can be facilitated by catalytically using a tertiary amine such as triethylmine, 1,4-diazabicyclo[2,2,2]octane and the like or a tin compound such as dibutyltin dilaurate, dibutyltin diacetate and the like. These compounds can be used in an amount of 0.01–5% by weight based on the diisocyanate compound.

Examples of the isocyanate compound having a photo-dimerizable group include the isocyanate compounds represented by the formulas (VI) and (VII) shown below:

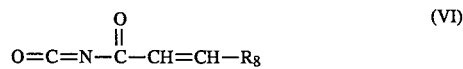

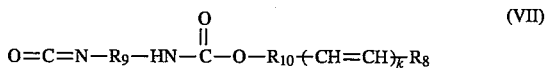

wherein $R_8$, $R_9$, $R_{10}$ and k are as define in formula (III).

The isocyanate compound represented by the above-mentioned formula (VII) is synthesized from a hydroxy compound having at least one photo-dimerizable group and an isocyanate compound. As the hydroxy compound having at least one photo-dimerizable group, for example, the compounds represented by the formula (VIII) shown below can be used. These hydroxy compounds can be used either singly or in combination of two or more members.

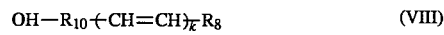

wherein $R_8$, $R_{10}$ and k are as defined in formula (III).

As the aromatic or heterocyclic group represented by $R_8$ in the formula (III), known groups can be used, among which the following ones are preferable:

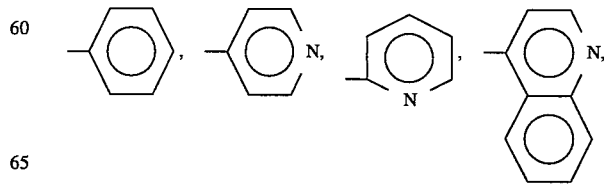

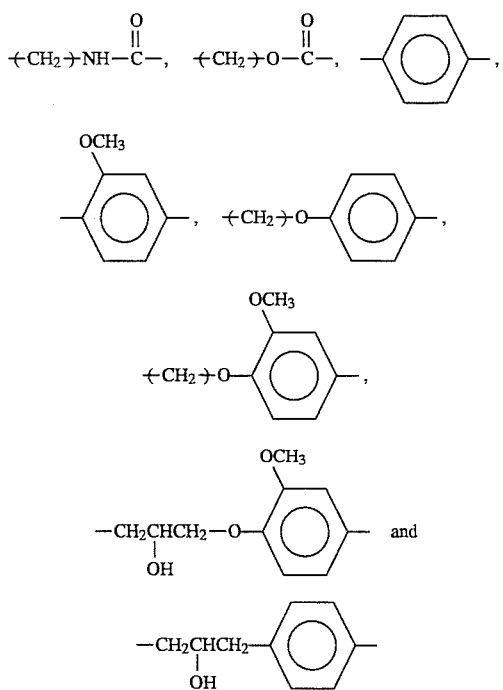

As the $R_{10}$, known groups can be used, among which divalent organic groups represented by the following formulas are preferable:

As the diisocyanate which reacts with the above-mentioned hydroxy compounds to give a monoisocyanate compound having a carbon-carbon double bond and a urethane bond in the molecule, the same diisocyanates as mentioned above can be used.

The diamino compounds represented by the formula (I) can be obtained by reacting the above-mentioned various polyamino compounds with a variety of photopolymerizable, photodimerizable or photocrosslinkable isocyanate compounds to form an adduct. The reaction is carried out at a temperature of −60° C. to 30° C. and preferably at −50° C. to 10° C. If the reaction temperature is lower than −60° C., there is available no solvent suitable for the reaction. If the temperature exceeds 30° C., the reaction selectivity between the water present in the solvent and the isocyanate compound is deteriorated. Preferably, in this reaction, the ratio between the polyamino compound and the isocyanate is controlled so as to leave unreacted two of the amino groups in the polyamino compound molecule. For example, when the polyamino compound is a tetraamine, the molar ratio of polyamino compound to isocyanate compound having photopolymerizable, photo-dimerizable or photocrosslinkable group is preferably adjusted to 0.9/2 to 1.2/2, and particularly preferably to 1/2.

When the polyamino compound is a triamine, the molar ratio of polyamino compound to the isocyanate compound having a photopolymerizable, photodimerizable or photocrosslinkable group is preferably adjusted to 0.9/1 to 1.1/1, and particularly preferably to 1/1. If the molar ratio exceeds this range, the reaction between polyamino compound and isocyanate compound tends to form an undesirable by-product. According to one of the particularly preferred embodiments of this production process, one mole of a monoisocyanate compound having a photopolymerizable, photodimerizable or photocrosslinkable group is reacted at a temperature of −50° C. to 0° C. with one mole of either one amino group of a polyamino compound in which two amino groups are separately linked to two atoms, adjacent to each other, in an aromatic or cycloalkyl ring, whereby only one of the two amino groups separately linked to two adjacent atoms in an aromatic or cycloalkyl ring can be reacted with the monoisocyanate compound with a relatively high selectivity. As a result, a diamino compound which is the intended reaction product can be obtained in a high yield.

Since an isocyanate compound readily reacts with a trace amount of water present in the reaction system to form an undesirable product, a lower reaction temperature is more desirable from the viewpoint of preventing this side reaction.

Beside the above, the diamino compound represented by formula (I) can be synthesized by using various starting compounds and combining known reactions in accordance with the intended objective diamino compound. For example, a compound of the following formula:

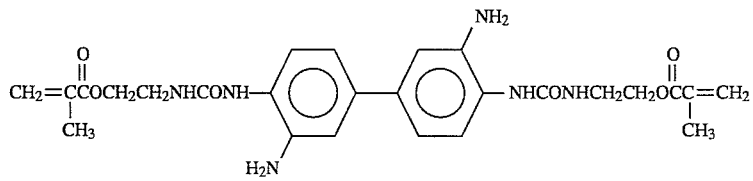

can be synthesized in the following manner by the use of 3,3'-dinitrobenzidine:

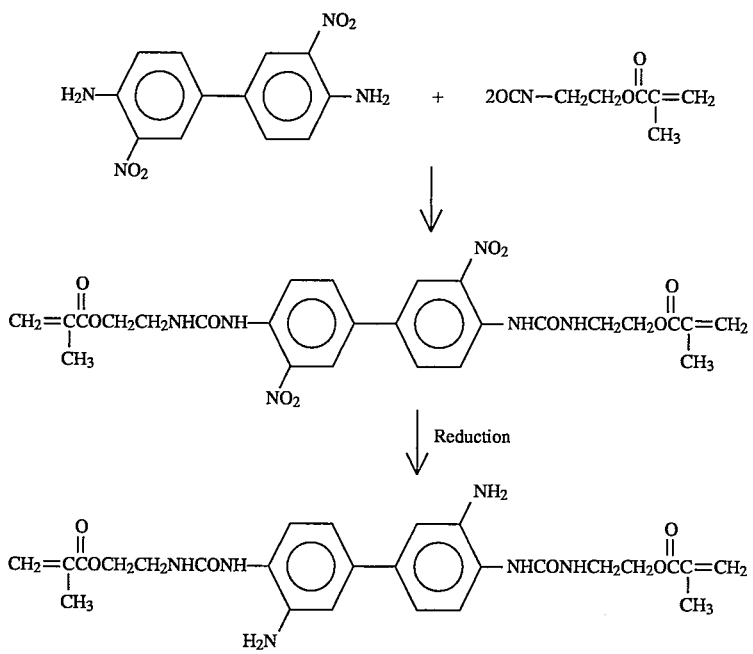

The diamino compound of the formula (I) obtained in the above-mentioned manner is useful as a constituent monomer of a poly(amic acid) resin having recurring units of the following formula (II):

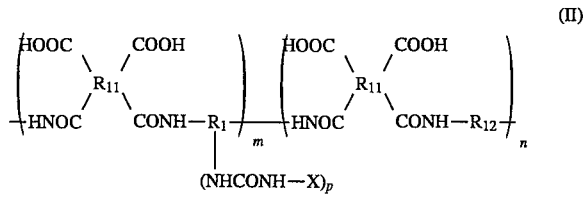

wherein X is a monovalent photosensitive group; $R_1$ is a (2+p)-valent organic group; $R_{11}$ is a tetravalent organic group; $R_{12}$ is a divalent organic group; p is an integer of 1 to 12; and m and n are molar numbers of recurring units provided that m/n is 1/99 to 100/0, or a poly(amic acid) ester resin prepared by esterifying its carboxyl group(s), or a polyimide resin prepared by a dehydrating or alcohol-eliminating ring-closure of these resins.

Preferably, in the formula (II), a portion smaller than 50% by mole of $R_{11}$ is a group represented by the following formula:

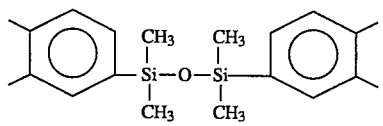

from the viewpoint of light transmission, solubility and adhesive property. If its 50% or more is the group of the above-mentioned formula, heat resistance and the like tend to become lower.

In the formula (II), when p=1, the one —(NHCONH—X) group and one of the two amide bonds are separately linked to two adjacent atoms in $R_1$, respectively. When p=2, the two —(NHCONH—X) groups are separately linked to two separate atoms in $R_1$ adjacent to two separate atoms too which the two amino groups are linked, respectively. When p is 3 or more, each —(NHCONH—X) group is linked to each atom in $R_1$ in addition to the manner when p=2.

The structural relationship of the linkages mentioned above results in that, when $R_1$ is a benzene ring and p=1, the one —(NHCONH—X) group and one of the two amide bonds are in a positional relationship of ortho to each other. On the other hand, when $R_1$ is a benzene ring and p=2, in the first pair consisting of one —(NHCONH—X) group and one amide bond, they are in a positional relationship of ortho to each other, and in the second pair consisting of the other —(NHCONH—X) group and the other amide bond, they are also in another positional relationship of ortho to each other. Owing to such positional relationships, a ring-closure reaction can take place and an imidazopyrrolone structure can be formed when the system is heated afterwards.

The poly(amic acid) resin having the recurring unit of formula (II) can be produced (a) by reacting a diamino compound of the formula (I) or a diamino compound mixture containing it with a tetracarboxylic acid dianhydride in an organic solvent [hereinafter, this process is sometimes referred to as "Process (a)"].

In the process (a), other diamino compounds may optionally be used in addition to the diamino compound of the formula (I), if desired. Preferable examples of said "other diamino compounds" include aromatic diamino compounds such as p-phenylenediamine, m-phenylenediamine, p-xylylenediamine, m-xylylenediamine, 1,5-diaminonaphthalene, 3,3'-dimethylbenzidine, 3,3'-dimethoxybenzidine, 4,4'- (or 3,4'-, 3,3'-, 2,4'- or 2,2'-) diaminodiphenylmethane, 4,4'- (or 3,4'-, 3,3'-, 2,4'- or 2,2'-) diaminodiphenyl ether, 4,4'- (or 3,4'-, 3,3'-, 2,4'- or 2,2'-) diaminodiphenyl sulfone, 4,4'- (or 3,4'-, 3,3'-, 2,4'- or 2,2'-) diaminodiphenyl sulfide, 4,4'-benzophenonediamine, 4,4'-di(4-aminophenoxy)phenyl sulfone, 1,1,1,3,3,3-hexafluoro-2,2-bis(4-aminophenyl)propane, 1,1,1,3,3,3-hexafluoro-2,2-bis[4-(4-aminophenoxy)phenyl]-propane, 2,2-bis[4-(4-aminophenoxy)phenyl]-propane, 3,3'-dimethyl-4,4'-diaminodiphenylmethane, 3,3',5,5'-tetramethyl-4,4'- diaminodiphenylmethane, 4,4'-di(3-aminophenoxy)phenyl sulfone, 3,3'-diaminodiphenyl sulfone, 2,2-bis(4-aminophenyl)-propane, the diamines represented by the formula shown below and the like; and alicyclic diamino compounds prepared by hydrogenating these aromatic diamino compounds;

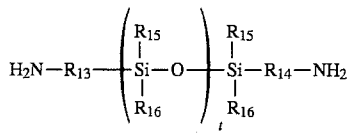

wherein $R_{13}$ and $R_{14}$ are independently a divalent hydrocarbon group; $R_{15}$ and $R_{16}$ are independently a monovalent hydrocarbon group; and t is an integer of 1 or greater. Although these diamino compounds may be used either singly or in combination of two or more of them, 4,4'-diaminodiphenyl ether is preferable from the viewpoint of heat resistance, mechanical properties and cost.

Preferable examples of said tetracarboxylic acid dianhydride include aromatic tetracarboxylic acid dianhydrides such as pyromellitic dianhydride, 3,3',4,4'-benzophenonetetra-carboxylic acid dianhydride, 3,3',4,4'-biphenyltetracarboxylic acid dianhydride, 1,2,5,6-naphthalenetetracarboxylic acid dianhydride, 2,3,6,7-naphthalenetetracarboxylic acid dianhydride, 2,3,5,6-pyridinetetracarboxylic acid dianhydride, 1,4,5,8-naphthalenetetracarboxylic acid dianhydride, 3,4,9,10-perylenetetracarboxylic acid dianhydride, 4,4'-sulfonyldiphthalic acid dianhydride, m-terphenyl-3,3",4,4"-tetracarboxylic acid dianhydride, p-terphenyl-3,3",4,4"-tetracarboxylic acid dianhydride, 4,4'-oxydiphthalic acid dianhydride, 1,1,1,3,3,3-hexafluoro-2,2-bis(2,3- or 3,4-dicarboxyphenyl)-propane dianhydride, 2,2-bis(2,3- or 3,4-dicarboxyphenyl)-propane dianhydride, 2,2-bis[4-(2,3- or 3,4-dicarboxyphenoxy) phenyl]-propane dianhydride, 1,1,1, 3,3,3-hexafluoro-2,2-bis[4-(2,3- or 3,4-dicarboxyphenoxy)phenyl]-propane dianhydride, tetracarboxylic acid dianhydrides represented by the following formula:

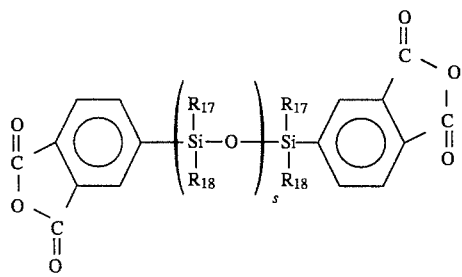

wherein $R_{17}$ and $R_{18}$ are independently a monovalent hydrocarbon group; and s is 0 or an integer of 1 or greater; hydrogenated products of these aromatic tetracarboxylic acid dianhydrides; and alicyclic tetracarboxylic acid dianhydrides of which examples are represented by the following formulas:

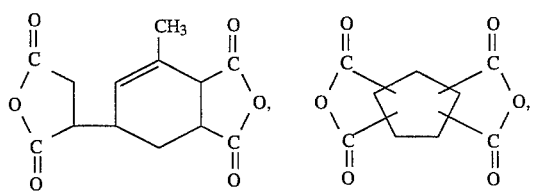

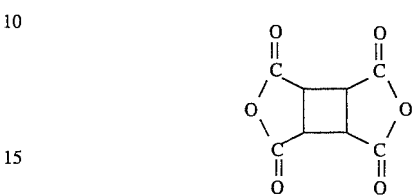

Needless to say, the benzene rings of the above-mentioned tetracarboxylic acid dianhydrides may optionally be substituted by a substituent such as alkyl group and the like. In addition to the tetracarboxylic acid dianhydride, aliphatic tetracarboxylic acid dianhydrides can also be used so far as their use does not deteriorate the heat resistance and mechanical properties.

The temperature of the reaction between the diamino compound represented by the formula (I), the optionally used diamino compound and the tetracarboxylic acid dianhydride is preferably 0°–100° C., and more preferably 5°–70° C. If the temperature is lower than 0° C., the tetracarboxylic acid dianhydride is quite difficult to dissolve. If the temperature exceeds 100° C., a reaction between the tetracarboxylic acid dianhydride and water present in the reaction medium readily takes place, and further an imidization reaction readily takes place in addition to the polycondensation reaction. As the amine component, other diamino compound may optionally be used in an amount of 0–99%, if desired. Preferably, the amine component consisting of the diamino compound represented by the formula (I) and the optionally used diamino compound and the tetracarboxylic acid dianhydride component are used at a ratio of 1/1.2 to 1/0.8 as expressed by a molar ratio of the former to the latter. More preferably, the two components are used at an equimolar ratio. If the molar ratio exceeds this range, a product of high molecular weight is difficult to obtain.

According to another preferable process for producing a poly(amic acid) resin having the recurring unit of formula (II), an isocyanate compound having a photopolymerizable, photodimerizable or photocrosslinkable group is added to a solution of a polyamino compound in an organic solvent and reacted to form an adduct, then the optionally used diamino compound is dissolved into the solution of the adduct in organic solvent thus obtained, and further a powdery tetracarboxylic acid dianhydride is added thereto and reacted [hereinafter, this process is sometimes referred to as "Process (b)"].

The temperature of the reaction between the polyamino compound and the isocyanate compound having a photopolymerizable, photodimerizable or photocrosslinkable group is preferably −60° C. to 30° C., and more preferably −50° C. to 10° C. If the temperature is lower than −60° C., there is available no solvent suitable for this reaction. If the temperature exceeds 30° C., the reaction selectivity between the isocyanate compound and the water present in the reaction solvent is deteriorated. The temperature of the reaction between the adduct formed above, the optionally used diamino compound and the tetracarboxylic acid dianhydride is preferably 0°–100° C., and more preferably 5°–70° C. If the temperature is lower than 0° C., the tetracarboxylic acid dianhydride is quite difficult to dissolve. If the temperature exceeds 100° C., the reaction between the tetracarboxylic acid dianhydride and the water present in reaction solvent readily takes place, and an imidization reaction readily takes place in addition to the polycondensation reaction. In order to obtain the above-mentioned adduct, it is preferable to adjust the ratio of polyamino compound to isocyanate compound having a photopolymerizable, photodimerizable or photocrosslinkable group so that two amino groups are left unreacted in the molecule of polyamino compound after the polyamino compound has been reacted with the isocyanate compound. For example, when the polyamino compound is a tetraamine, the molar ratio of the polyamino compound to the isocyanate compound having a photopolymerizable, photodimerizable or photocrosslinkable group is preferably adjusted to 0.9/2 to 1.1/2, and more preferably to 1/2.

When the polyamino compound is a triamine, the molar ratio of the polyamino compound to the isocyanate compound having a photopolymerizable, photodimerizable or photocrosslinkable group is preferably adjusted to 0.9/1 to 1.1/1, and more preferably to 1/1. If the molar ratio exceeds this range, a reaction takes place between the polyamino compound and the isocyanate compound to form an undesirable by-product. As the amine component, other diamino compound may optionally be used in an amount of 0–99%, if desired. The amine component consisting of the polyamino compound and the optionally used diamino compound and the tetracarboxylic acid dianhydride component are used preferably at a ratio of 1/1.2 to 1/0.8 as expressed in terms of molar ratio of the former to the latter, and more preferably at an equimolar ratio. If the molar ratio exceeds this range, a product of high molecular weight is difficult to obtain. According to one preferred embodiment of Process (b), one mole of a monoisocyanate compound having a photopolymerizable, photodimerizable or photocrosslinkable group is reacted at −50° C. to 0° C. with one mole of either one amino group of the polyamino compound in which two amino groups are separately linked to two atoms, adjacent to each other, in the aromatic or cycloalkyl ring, and thereafter a tetracarboxylic acid dianhydride is reacted therewith. By this process, only one of the two amino groups separately linked to two atoms in the aromatic or cycloalkyl ring can be reacted with the monoisocyanate compound with a relatively high selectivity. As a result, for example, a diamino compound having a photopolymerizable, photodimerizable or photocrosslinkable group represented by the formula shown below can be obtained easily. The poly(amic acid) finally obtained therefrom can be made into a high-molecular weight polymer of a nearly linear structure without undesirable gelation nor termination of polymerization:

be adopted from the viewpoint of preventing this side reaction.

According to yet another preferable production process, a solution of a tetracarboxylic acid dianhydride in an organic solvent is added to a solution of a polyamino compound and an optionally used diamino compound in an organic solvent and reacted to form a polycondensate, and then an isocyanate compound having a photopolymerizable, photodimerizable or photocrosslinkable group is added to a solution of said polycondensate in an organic solvent and reacted [hereinafter, this process is sometimes referred to as "Process (c)"]. In this process, the temperature of the reaction is preferably −60° C. to 100° C., and more preferably −50° C. to 60° C. If the temperature is lower than −60° C., the reaction product becomes highly viscous as the reaction progresses, and the stirring becomes quite difficult to practice. If the reaction temperature exceeds 100° C., gelation readily takes place. In order to prevent the gelation and obtain a high-molecular weight product, it is preferable to adopt a relatively low reaction temperature in the above-mentioned range.

In the Process (c), the amine component consisting of the polyamino compound and the optionally used diamino compound and the tetracarboxylic acid dianhydride component which are used for the purpose of obtaining a polycondensate are preferably used at a ratio of 1/1.2 to 1/0.8, and more preferably 1/1, as expressed in terms of molar ratio of the former to the latter. If the molar ratio exceeds this range, a product of high molecular weight is difficult to obtain or gelation takes place readily. Preferably, the isocyanate compound having a photopolymerizable, photodimerizable or photocrosslinkable group is used in an amount of 5–100% by mole based on the amino group of the polycondensate. As the amine component, other diamino compound may optionally be used in an amount of 0–99%, if desired.

As the process for producing a poly(amic acid) resin represented by formula (II), Process (a) is particularly preferable because it can give a high-molecular weight poly(amic acid) resin excellent in mechanical properties without gelation and it facilitates to form a high solid poly(amic acid) resin solution advantageously usable for forming a thick film.

As the process for producing a poly(amic acid) ester resin in which the carboxyl group of the above-mentioned poly(amic acid) resin having the recurring unit represented by the formula (II) is esterified, there can be referred to a process which comprises subjecting a diamino compound of formula (I), an optionally used diamino compound and a tetracarboxylic acid diester having been esterified by a desired organic group having no photosensitive group to a condensation reaction according to a known method, for example a method using a condensing agent such as dicy-

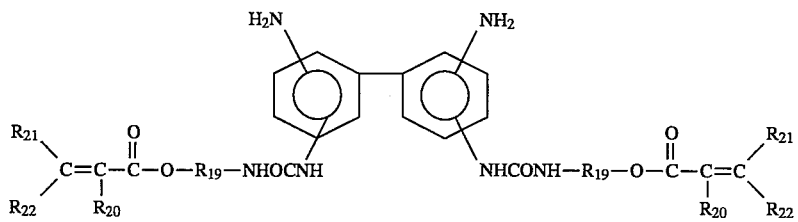

wherein $R_{19}$ is a divalent alkyl group; and $R_{20}$, $R_{21}$ and $R_{22}$ are independently a hydrogen atom or an alkyl group.

Since an isocyanate compound readily reacts with a trace amount of water present in the reaction system to form an undesirable by-product, a lower reaction temperature should clohexylcarbodiimide, phosphinedisulfide, thionyl chloride or the like. As said organic group having no photosensitive group which can be used for esterifying the carboxyl group of the poly(amic acid), a variety of ones can be referred to, among which those which can be eliminated at a relatively low temperature and can rapidly complete the ring-closure reaction at elevated temperature are particularly preferable. It is also possible to produce the poly(amic acid) ester resin by esterifying carboxyl groups of the poly(amic acid) resin having recurring units of the formula (II) using a compound having no vinyl group.

From the poly(amic acid) represented by formula (II) which has been obtained according to the Process (a), Process (b) or Process (c) mentioned above, a polyimide resin can be obtained by a conventional method of dehydrating ring-closure, such as a thermal ring-closure reaction, a chemical ring-closure reaction using acetic anhydride/pyridine or the like, a ring-closure reaction using an isocyanate, and the like. The conversion of a poly(amic acid) acid to the corresponding polyimide is accompanied by a decrease in the solubility in the organic solvent used for the reaction. Accordingly, it is preferable that the diamino compound of the formula (I), the optionally used diamino compound and the tetracarboxylic acid dianhydride used as starting materials in production of the polyimde are those capable of forming a polyimide resin soluble in the organic solvent used in the reaction.

As the organic solvent used in the above-mentioned reaction, polar solvents in which the resulting poly(amic acid) resin, the poly(amic acid) ester resin or the polyimide resin can be dissolved completely are generally preferable. Examples of such polar solvent include N-methyl-2-pyrrolidone, N,N-dimethylacetamide, N,N-dimethylformamide, dimethyl sulfoxide, tetramethylurea, hexamethylphosphoric acid triamide, γ-butyrolactone and the like. Apart from these polar solvents, usual organic solvents including ketones, esters, lactones, ethers, halogenated hydrocarbons and hydrocarbons can also be used, of which examples include acetone, methyl ethyl ketone, methyl isobutyl ketone, cyclohexanone, methyl acetate, ethyl acetate, butyl acetate, diethyl oxalate, diethyl malonate, γ-butyrolactone, diethyl ether, ethylene glycol dimethyl ether, diethylene glycol dimethyl ether, tetrahydrofuran, dichloromethane, 1,2-dichlorethane, 1,4-dichlorobutane, trichlorethane, chlorobenzene, o-dichlorobenzene, hexane, heptane, octane, benzene, toluene, xylene and the like.

The photosensitive resin composition of this invention comprises (A) a poly(amic acid) resin having recurring units of the formula (II), a poly(amic acid) ester resin prepared by esterifying its carboxylic group and/or a polyimide resin prepared by a dehydrating or alcohol-eliminating ring-closure reaction thereof, and (B) an optionally used photo initiator.

Examples of said optionally used photo initiator include Michler's ketone, benzoin, 2-methylbenzoin, benzoin methyl ether, benzoin ethyl ether, benzoin isopropyl ether, benzoin butyl ether, 2-t-butylanthraquinone, 1,2-benzo-9,10-anthraquinone, anthraquinone, methylanthraquinone, 4,4'-bis(diethylamino)-benzophenone, acetophenone, benzophenone, thioxanthone, 1,5-acenaphthene, 2,2-dimethoxy-2-phenylacetoacetophenone, 1-hydroxycyclohexyl phenyl ketone, 2-methyl-[4-(methylthio)phenyl]-2-morpholino-1-propanone, diacetyl, benzil, benzil dimethyl ketal, benzil diethyl ketal, diphenyl disulfide, anthracene, phenanthrenequinone, riboflavin tetrabutyrate, Acridine Orange, erythrosine, 2-isopropylthioxanthone, 2,6-bis(p-diethylaminobenzylidene)-4-methyl-4-azacyclopentanone, 6-bis(p-dimethylamino)-cyclopentanone, 2,6-bis(p-diethylaminobenzylidene)-4-phenylcyclohexanone, 1-phenyl-1,2-propanedione-2-(o-ethoxycarbonyl)-oxime, 7-diethylamino-4-methylcoumarin, 2-(p-dimethylaminostyryl)-benzoxazole, 3,3',4,4'-tetrakis(t-butyldioxycarbonyl)-benzophenone, aminostyryl ketone represented by the following formula (X), 3-carbonyl-substituted biscoumarin compounds represented by the following formula (XI), and the like:

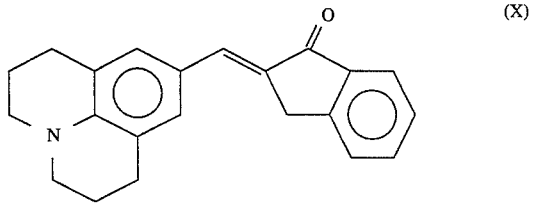

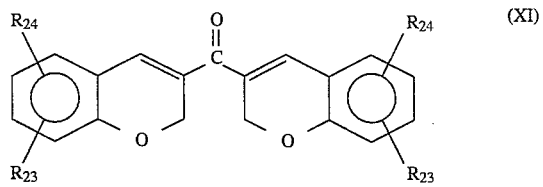

wherein $R_{23}$ and $R_{24}$ are independently a hydrogen atom, an alkoxy group or a dialkylamino group.

These photoinitiators can be used either singly or in combination of two or more of them. The photoinitiator is used preferably in an amount of 0.01–30 parts by weight, more preferably in an amount of 0.1–10 parts by weight, per 100 parts by weight of the poly(amic acid) resin, poly(amic acid) ester resin and/or polyimide resin or the sum of these resins and a polymerizable unsaturated compound, from the viewpoint of sensitivity of photosensitive resin composition and heat resistance of coating film. If the amount is smaller than 0.01 part by weight, the effect cannot be exhibited explicitly. If it exceeds 30 parts by weight, heat resistance and film properties of the cured film tend to be deteriorated.

A photocoinitiator such as amines, amino acids and the like may be additionally used in combination with these photo initiators. Examples of said amine include ethyl p-dimethylaminobenzoate, isoamyl p-dimethylaminobenzoate, p-dimethylaminobenzonitrile, ethyl N,N-dimethylanthranilate and the like. Examples of said amino acid include N-methyl-N-(p-chlorophenyl)-glycine, N-phenylglycine, N-ethyl-N-(p-chlorophenyl)-glycine, N-(n-propyl)-N-(p-chlorophenyl)-glycine, N-methyl-N-(p-bromophenyl)-glycine, N-ethyl-N-(p-bromophenyl)-glycine, N-(p-cyanophenyl)-glycine, N-(p-chlorophenyl)-glycine, N-(p-bromophenyl)-glycine and the like.

In order to improve the heat stability of the photosensitive resin composition, a known thermal polymerization inhibitor may be incorporated into the composition. Examples of said polymerization inhibitor include p-methoxyphenol, hydroquinone, t-butylcatechol, pyrogallol, phenothiazine, chloranil, naphthylamine, β-naphthol, 2,6-di-t-butyl-p-cresol, pyridine, nitrobenzene, p-toluidine, Methylene Blue, 2,2-methylenebis-(4-methyl-6-t-butylphenol), 2,2'-methylenebis(4-ethyl-6-t-butylphenol); 2,5-diphenyl-p-benzoquinone; N-nitroso compounds such as N-nitroso-N-arylhydroxylamine ammonium salt represented by the following formula:

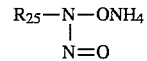

wherein $R_{25}$ is phenyl or naphthyl group, N-nitrosodiphenylamine, N,N-dimethylnitrosoaniline, N,N-diethylnitrosoaniline, N-nitrosodiethylamine, nitrosodimethylaminophenol, nitrosodiethyl-aminophenol, N-nitroso-N-methylaniline, N-nitroso-N-phenylhydroxylamine, nitrosohydroxyquinoline, dinitrosopentamethylenetetramine and the like; and C-nitroso compounds such as nitrosobenzene, 2-nitrosotoluene, 9-nitrosophenol, 4-nitrosoresorcinol-1-monomethyl ether, 2-nitroso-5-dimethylaminophenol, p-nitroso-N,N-dimethylamine, p-nitroso-N,N-diethylamine, 1-nitroso-2-naphthol, 2-nitroso-1-naphthol, 5-nitroso-8-hydroxyquinoline, 2-nitroso-1-naphthol-4-sulfonic acid, sodium 1-nitroso-2-naphthaol-3,6-disulfonate, 2-nitroso-5-(N-ethyl-N-sulfopropylamino)-phenol and the like.

These thermal polymerization inhibitors may be used either singly or in combination of two or more of them. Preferably, they are used in an amount of 0.001–10 parts by weight per 100 parts by weight of the remainder left after deducting polymerization inhibitor, organic solvent and photo initiator from the photosensitive resin composition. If the amount is smaller than 0.001 part by weight, no explicit polymerization inhibiting effect can be achieved. If the amount exceeds 10 parts by weight, the photocurability of the composition tends to be deteriorated.

If desired, the photosensitive resin composition of this invention may contain a polymerizable unsaturated compound. The polymerizable unsaturated compounds usable for this purpose include a variety of compounds, among Which acrylic acid type and methacrylic acid type compounds are practically preferable. Examples of said acrylic acid type compound include acrylic acid, methyl acrylate, ethyl acrylate, n-propyl acrylate, isopropyl acrylate, n-butyl acrylate, isobutyl acrylate, cyclohexyl acrylate, benzyl acrylate, carbitol acrylate, methoxyethyl acrylate, ethoxyethyl acrylate, butoxyethyl acrylate, hydroxyethyl acrylate, hydroxypropyl acrylate, butylene glycol acrylate, N,N-dimethylaminoethyl acrylate, N,N-diethylaminoethyl acrylate, glycidyl acrylate, tetrahydrofurfuryl acrylate, pentaerythritol monoacrylate, trimethylolpropane monoacrylate, allyl acrylate, 1,3-propylene glycol diacrylate, 1,4-butylene glycol diacrylate, 1,6-hexane glycol diacrylate, neopentyl glycol diacrylate, dipropylene glycol diacrylate, 2,2-bis(4-acryloxydiethoxyphenyl)-propane, 2,2-bis(4-acryloxypropoxyphenyl)propane, trimethylolpropane diacrylate, pentaerythritol diacrylate, trimethylolpropane triacrylate, pentaerythritol triacrylate, triacryl formal, tetramethylolmethane tetraacrylate, tris(2-hydroxyethyl)-isocyanuric acid acrylate, the compounds represented by the following formulas:

$$H_2C=CH-\underset{\underset{O}{\|}}{C}+OCH_2CH_2)_b\!-O-\underset{\underset{O}{\|}}{C}-CH=CH_2$$

wherein b is an integer of 1–30,

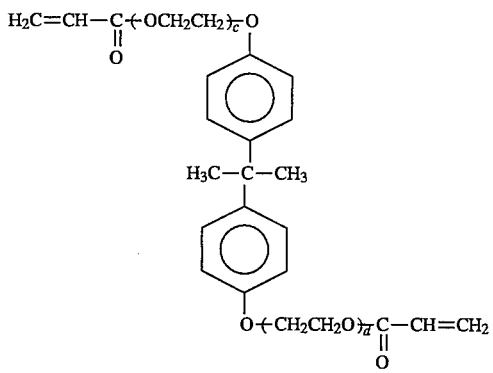

wherein c and d are integers selected so that (c+d) becomes equal to 2–30,

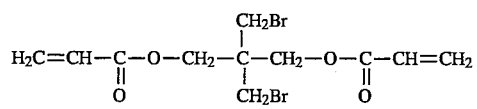

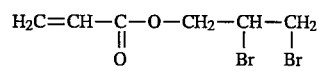

Examples of said methacrylic acid type compound include methacrylic acid, methyl methacrylate, ethyl methacrylate, propyl methacrylate, isopropyl methacrylate, butyl methacrylate, isobutyl methacrylate, cyclohexyl methacrylate, benzyl methacrylate, octyl methacrylate, ethylhexyl methacrylate, methoxyethyl methacrylate, ethoxyethyl methacrylate, butoxyethyl methacrylate, hydroxyethyl methacrylate, hydroxypropyl methacrylate, hydroxybutyl methacrylate, hydroxypentyl methacrylate, N,N-dimethylaminomethacrylate, N,N-diethylamino-methacrylate, glycidyl methacrylate, tetrahydrofurfuryl methacrylate, methacryloxypropyltrimethoxysilane, allyl methacrylate, trimethylolpropane monomethacrylate, pentaerythritol monomethacrylate, 1,3-butylene glycol dimethacrylate, 1,6-hexane glycol dimethacrylate, neopentyl glycol dimethacrylate, 2,2-bis(4-methacryloxydiethoxyphenyl)-propane, trimethylolpropane dimethacrylate, pentaerythritol dimethacrylate, trimethylolpropane trimethacrylate, pentaerythritol trimethacrylate, tetramethylolmethane tetramethacrylate, tris(2-hydroxyethyl)-isocyanuric acid methacrylate, the compounds represented by the following formulas:

$$H_2C=\underset{\underset{CH_3}{|}}{C}-\underset{\underset{O}{\|}}{C}+OCH_2CH_2)_e\!-O-\underset{\underset{CH_3}{|}}{C}-C=CH_2$$

wherein e is an integer of 1–30,

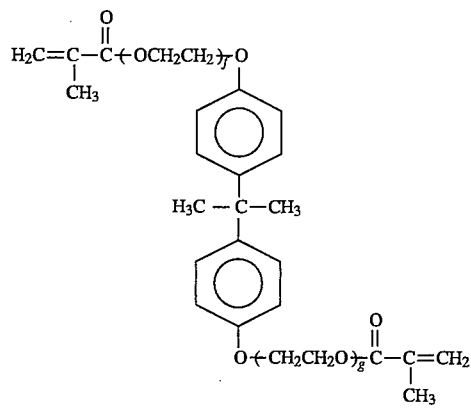

wherein f and g are integers selected so that (f+g) becomes equal to 1–30,

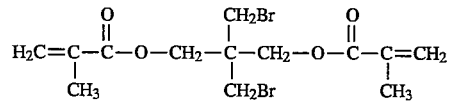

-continued $$H_2C=C(CH_3)-C(=O)-O-CH_2-CH(Br)-CH_2Br$$

Further, it is also possible to use butyl crotonate, glycerin monocrotonate, vinyl butyrate, vinyl trimethylacetate, vinyl caproate, vinyl chloroacetate, vinyl lactate, vinyl benzoate, divinyl succinate, divinyl phthalate, methacrylamide, N-methylmethacrylamide, N-ethylmethacrylamide, N-allyl-methacrylamide, N-hydroxyethyl-N-methyl-methacrylamide, acrylamide, N-t-butylacrylamide, N-methylolacrylamide, N-isobutoxymethylacrylamide, N-butoxymethylacrylamide, diacetoneacrylamide, hexyl vinyl ether, ethylhexyl vinyl ether, vinyl tolyl ether, polyvinyl ethers of polyhydric alcohols, styrene derivatives having a substituent such as alkyl, alkoxy, halogen, carboxyl, allyl or the like on the o- and p-positions, divinylbenzene, allyloxyethanol, diallyl esters of dicarboxylic acids, N-vinyloxazolidone, N-vinylimidazole, N-vinylpyrrolidone, N-vinylcarbazole and the like, and the compounds represented by the following formulas (XII)–(XV), and the like:

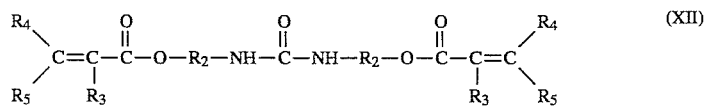
(XII)

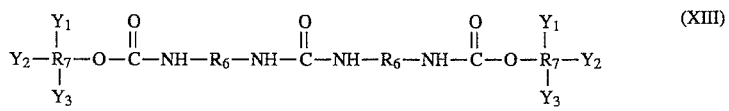
(XIII)

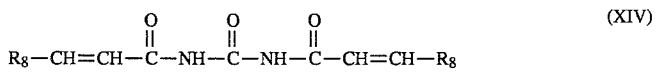
(XIV)

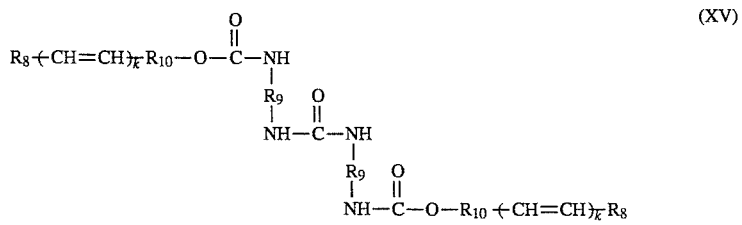
(XV)

wherein $R_2, R_3, R_4, R_5, R_6, R_7, R_8, R_9, R_{10}, Y_1, Y_2, Y_3$ and k are as defined above.

The above-mentioned polymerizable unsaturated compounds may be used either singly or in combination of two or more of them. Among these compounds, the compounds of the following formulas, wherein b is 2–9, are preferable. These compounds are excellent in photocurability and thermal decomposability and function as a dissolution-promotor of poly(amic acid), and therefore they can shorten the development time:

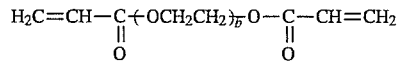

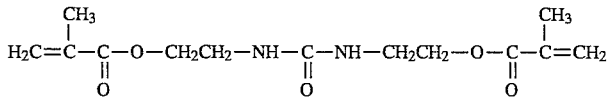

The polymerizable unsaturated compound is used preferably in an amount of 2–500 parts by weight and particularly preferably in an amount of 10–200 parts by weight, per 100 parts by weight of the poly(amic acid) resin, poly(amic acid) ester resin and/or the polyimide resin, from the viewpoint of solubility of prebaked film of the composition in a developer, photo-curability and heat resistance of coating film. If its amount is smaller than 2 parts by weight, the effect of shortening the developing time is insufficient. If its amount exceeds 500 parts by weight, the polymerizable unsaturated compound cannot sufficiently be thermally decomposed or volatilized and remains in the final cured film, which deteriorates the heat resistance of cured film. In addition, it occupies a great volume in the composition so that the composition becomes difficult to form into a thick film.

Into the photosensitive resin composition of this invention, one or more adhesion assistants such as silane coupler, aluminum chelating agent, titanium chelating agent and the like may additionally be incorporated, if desired. The order and method in which the ingredients are mixed are not critical, and the composition may be coated on a substrate such as a copper-clad laminate, a silicon wafer or the like by the method of dipping, spraying, screen printing, spinner coating or the like and then dried to form a coating film.

According to another adoptable embodiment, for example, the resin composition is coated on a flexible substrate such as polyester film and dried to form a laminate, a cover sheet of polyethylene or the like is provided thereon to form a dry film of sandwich structure, and then the cover sheet is peeled off to form a coating film on the substrate to be coated. The use of the cover sheet is not always indispensable.

The coating film thus formed is irradiated with active rays through a mask picturing a desired pattern, whereby a polymerization takes place in the irradiated area (exposed area) as a result of which the exposed area greatly decreases its solubility as compared with the unexposed area. As the active ray, ultraviolet light or visible light is used usually, though ionizing radiations such as electron beams, radiations and the like can also exercise a similar effect on the coating film.

The coating film having been treated in the above-mentioned manner is then treated with an appropriate developer, whereby the unexposed area retaining a high solubility is developed and removed while the exposed area of which solubility has been lowered by the irradiation with active light remains so that a desired resin pattern can be obtained. The developers which can be used include organic solvents and/or aqueous alkali solutions.

Examples of said organic solvent include polar solvents such as N-methylpyrrolidone, N-acetyl-2-pyrrolidone, N,N-dimethylformamide, N,N-dimethylacetamide, dimethyl sulfoxide, hexamethylene phosphoric triamide, γ-butyrolactone and the like. Mixtures of these polar solvents and water or general organic solvents including alcohols such as methanol, ethanol, isopropanol and the like, aromatic hydrocarbons such as toluene, xylene and the like, ketones such as acetone, methyl ethyl ketone, methyl isobutyl ketone and the like, esters such as ethyl acetate, methyl propionate and the like, and ether such as tetrahydrofuran, dioxane and the like are also usable.

The term "aqueous alkali solution" used herein means a solution prepared by dissolving a basic compound in water. As said basic compound, hydroxides, carbonates, bicarbonates, silicates, phosphates, pyrophosphates and acetates of alkali metals or quaternary ammoniums and amines are used. Specific examples of said basic compound include lithium hydroxide, sodium hydroxide, potassium hydroxide, ammonium hydroxide, trimethylbenzylammonium hydroxide, tetramethylammonium hydroxide, sodium carbonate, potassium carbonate, sodium hydrogen carbonate, sodium silicate, sodium phosphate, sodium pyrophosphate, sodium acetate, monoethanolamine, diethanolamine, triethanolamine and the like. These basic compounds are used usually in an amount of 0.0001–50 parts by weight and preferably in an amount of 0.001–30 parts by weight per 100 parts by weight of water. If the amount of basic compound is too small, developability is deteriorated. If the amount of the basic compound is too large, it cannot dissolve completely so that no uniform solution can be formed, or the developer has too high a viscosity, which both bring about a decrease in developability.

As the developer, an organic solvent and an aqueous alkali solution are used, either singly or in the form of a mixture thereof. When a mixture of an organic solvent and an aqueous alkali solution is used, the organic solvent is used usually in an amount of 0.1–100 parts by weight and preferably in an amount of 5–50 parts by weight per 100 parts by weight of the aqueous alkali solution. The use of aqueous alkali solution as the developer is preferable, because it is non-flamable and inexpensive.

The relief pattern which has been formed by the development is then washed with a rinsing solution to remove the developer. The pattern thus obtained is first preliminarily dried at 50°–250° C. and thereafter heated at 300°–400° C., i.e. post-cured, whereby a polyimidazopyrrolone resin or a polyimidazopyrroloneimide resin excellent in heat resistance and film strength and low in thermal expansion can be formed. They are useful as materials for surface protection, interlaminar insulation, etc. of semiconductors, multi-layer printed circuit boards, high-density mounting substrate and the like. Accordingly, the photosensitive resin composition of this invention is very useful mainly in the above-mentioned fields of fine processings.

Next, a preferred embodiment of the production of the polyimidazopyrrolone resin of this invention and a preferred embodiment of the production of the polyimidazopyrroloneimide resin of this invention are mentioned below.

① Polyimidazopyrrolone resin
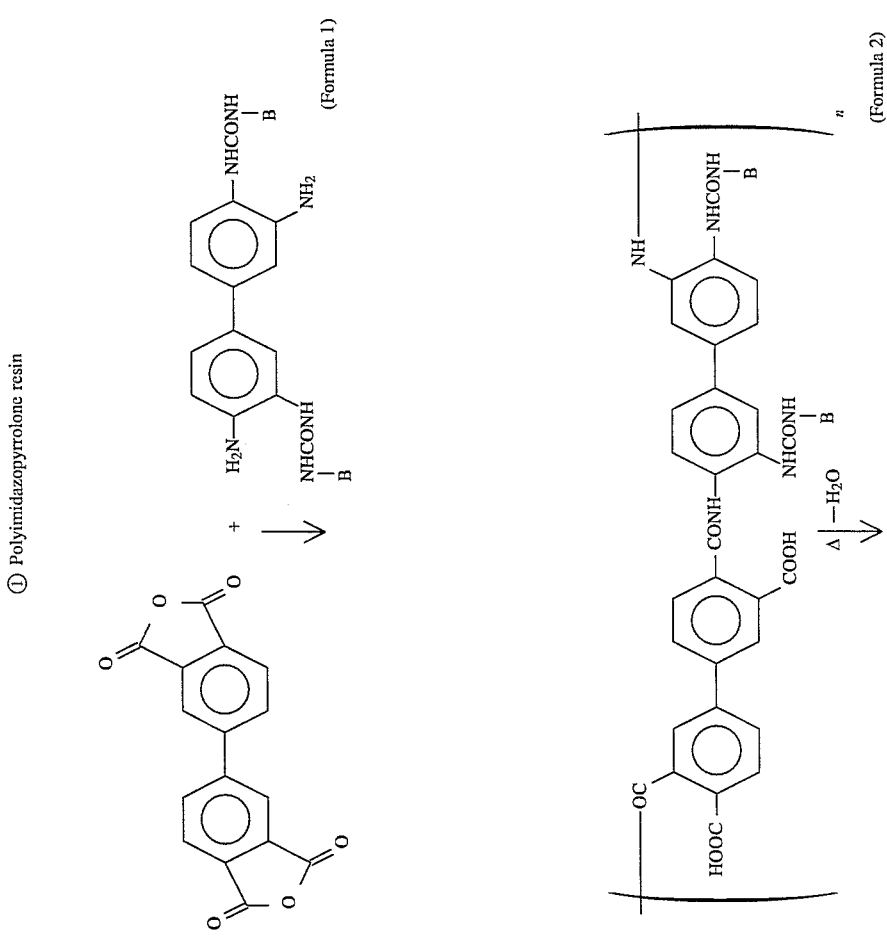

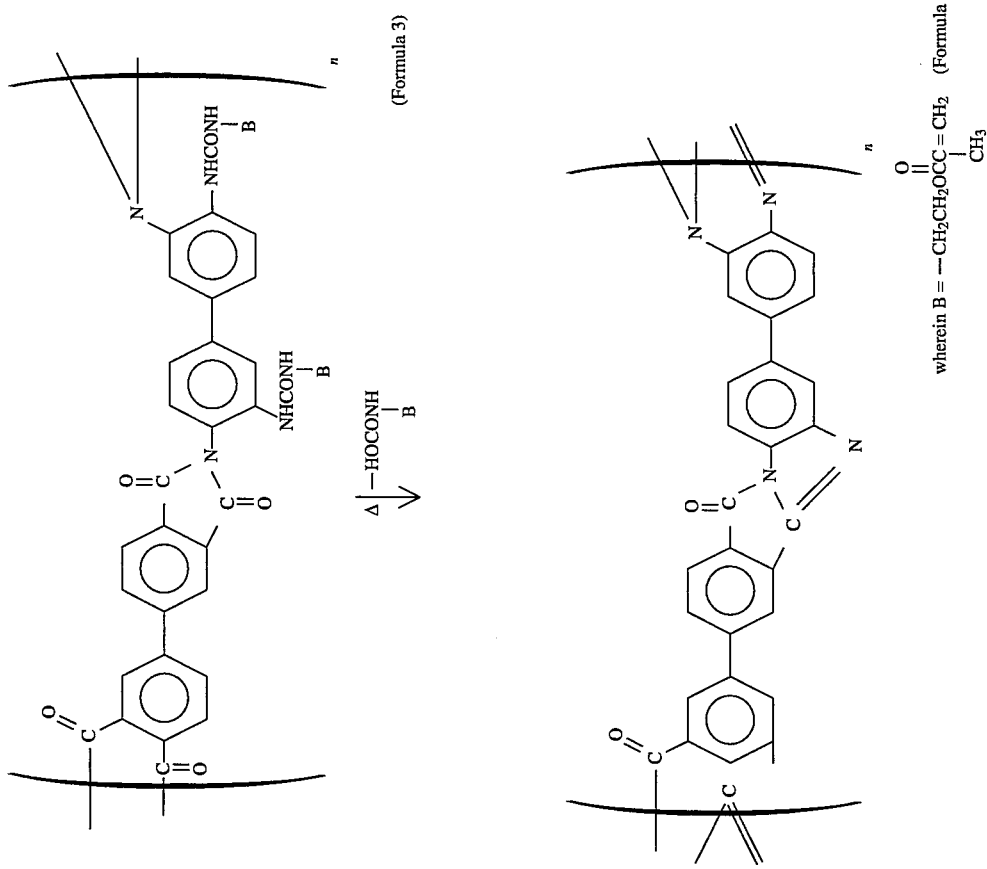

-continued
② Polyimidazopyrroloneimide resin
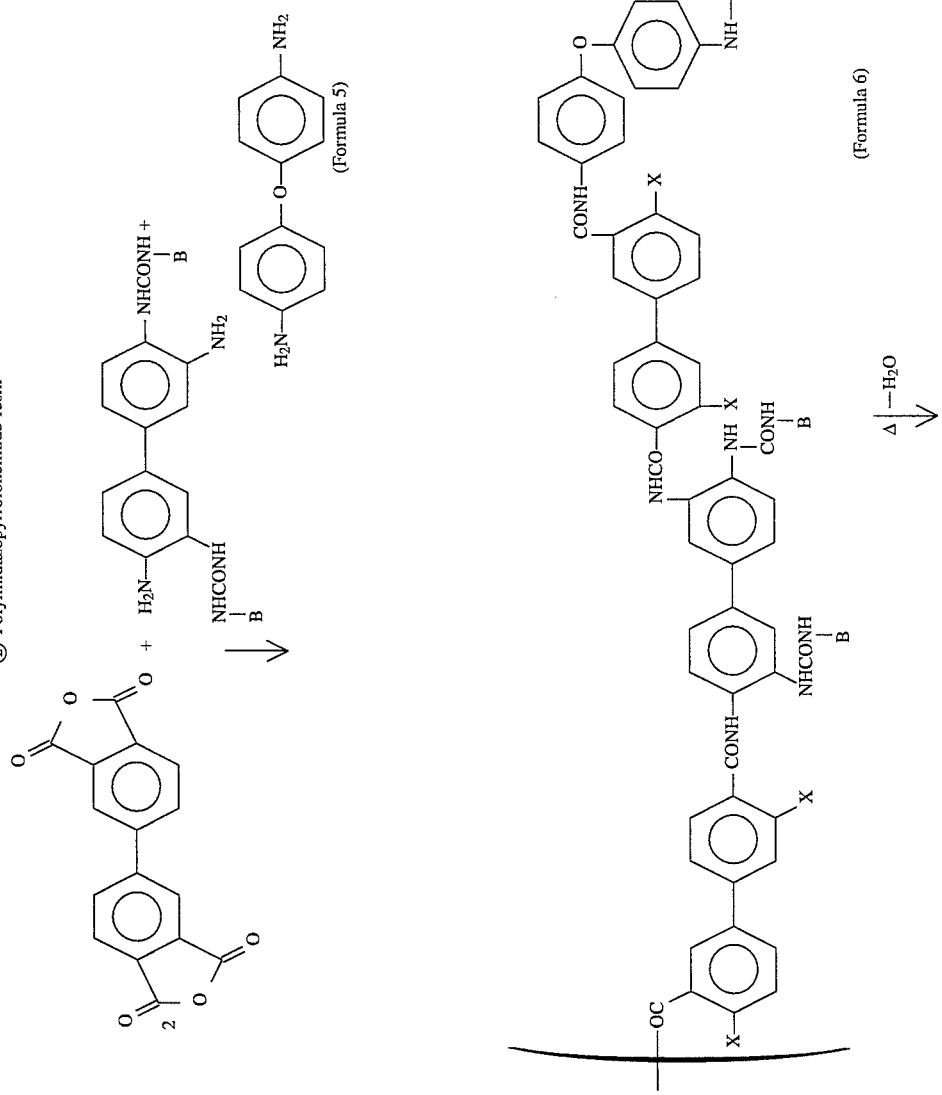
(Formula 5)
(Formula 6)

-continued
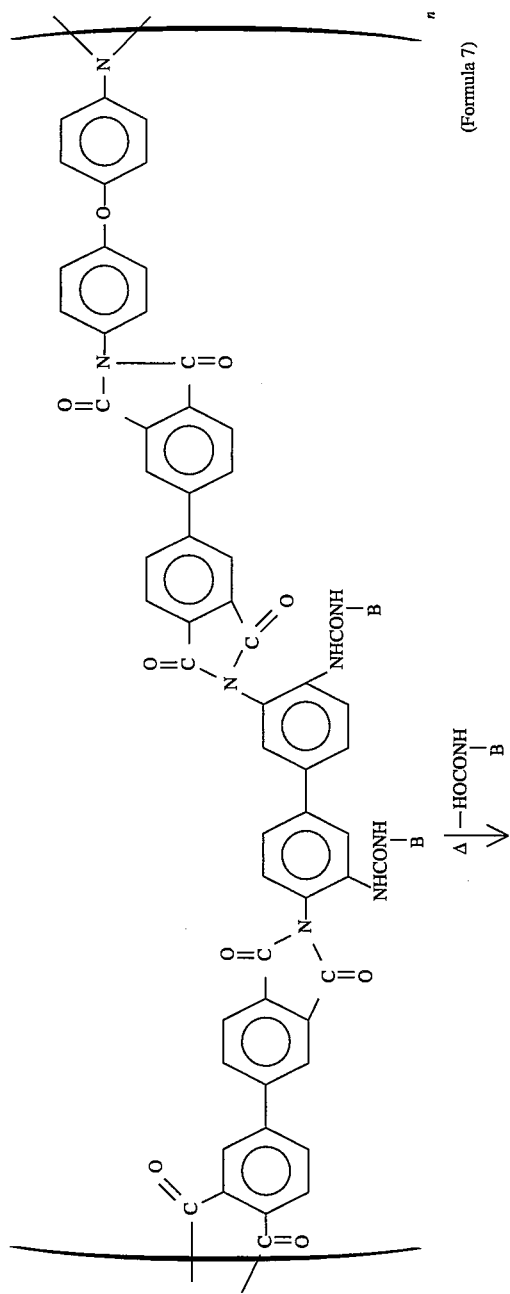
(Formula 7)

-continued
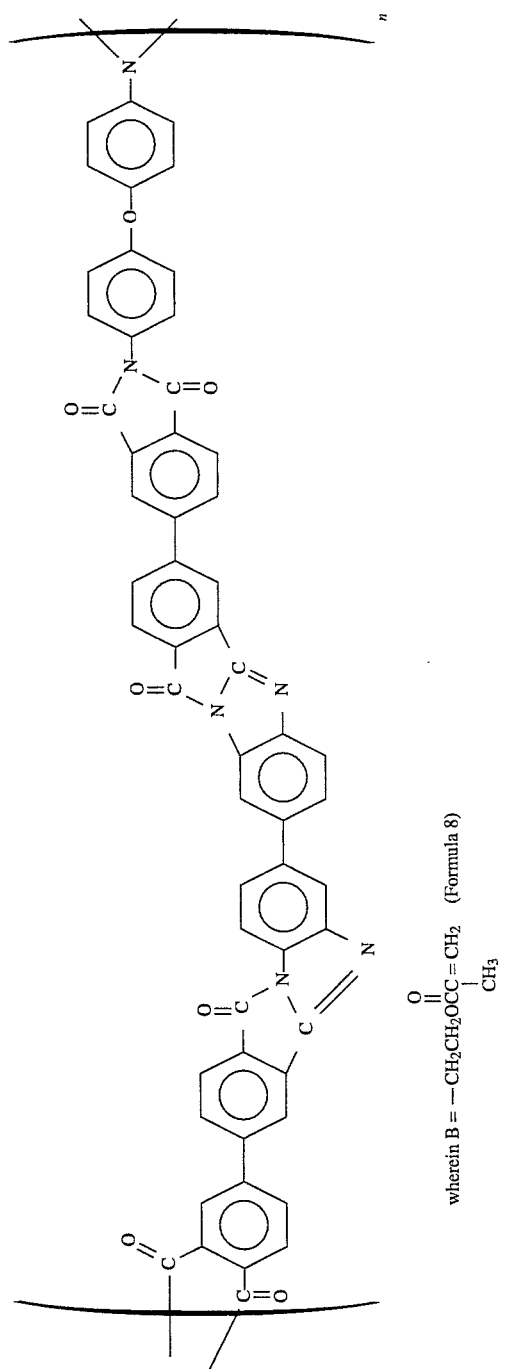
wherein B = —CH$_2$CH$_2$OCC=CH$_2$ (Formula 8)
                    ||  |
                    O  CH$_3$
X = —COOH In the scheme ①, elimination of the introduced photosensitive group, i.e. the group containing B, takes place in the process of conversion from the formula (3) to the formula (4). In the scheme ②, it takes place in the process of conversion from formula (7) to the formula (8).

Since the photosensitive group is bonded to the main chain through a urea bond which is much easier to eliminate as compared with conventionally used other bonds such as ester bond, the photosensitive group is eliminated instantly at the time of post-cure instead of being eliminated gradually. Thus, the finally cured film of this invention exhibits no loss in weight upon heating, or it exhibits an excellent heat stability.

Further, after the elimination of photosensitive group has taken place instantly, the pattern undergoes no deformation, and therefore the film of this invention is excellent in dimensional stability.

Next, this invention is illustrated with reference to the following Examples and Comparative Examples. This invention is by no means limited by these Examples.

SYNTHESIS EXAMPLE 1

Figure 2:
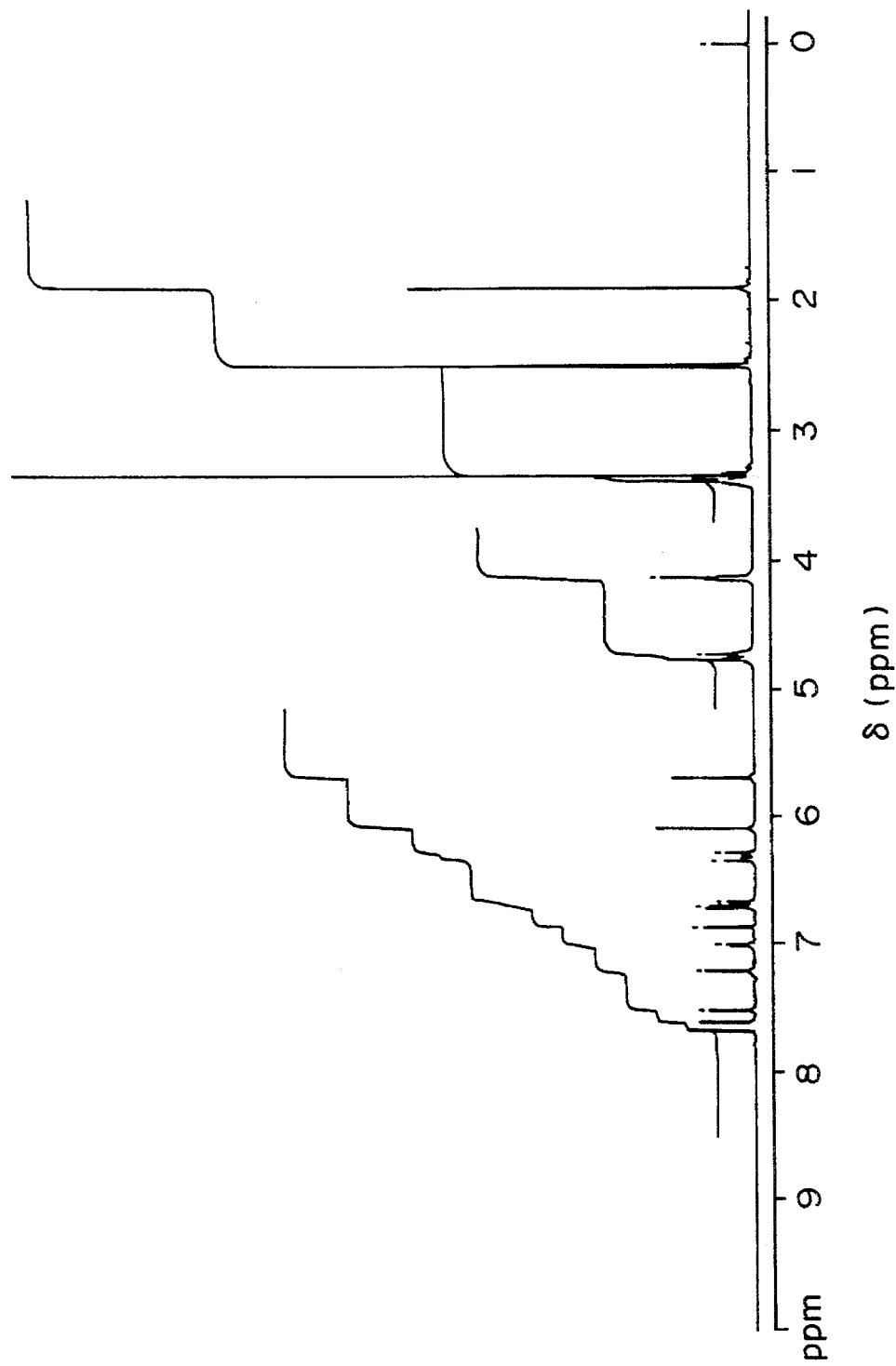
FIG. 2 is a $^1$H-NMR spectrum of the product obtained in Synthesis Example 1.
Figure 3:
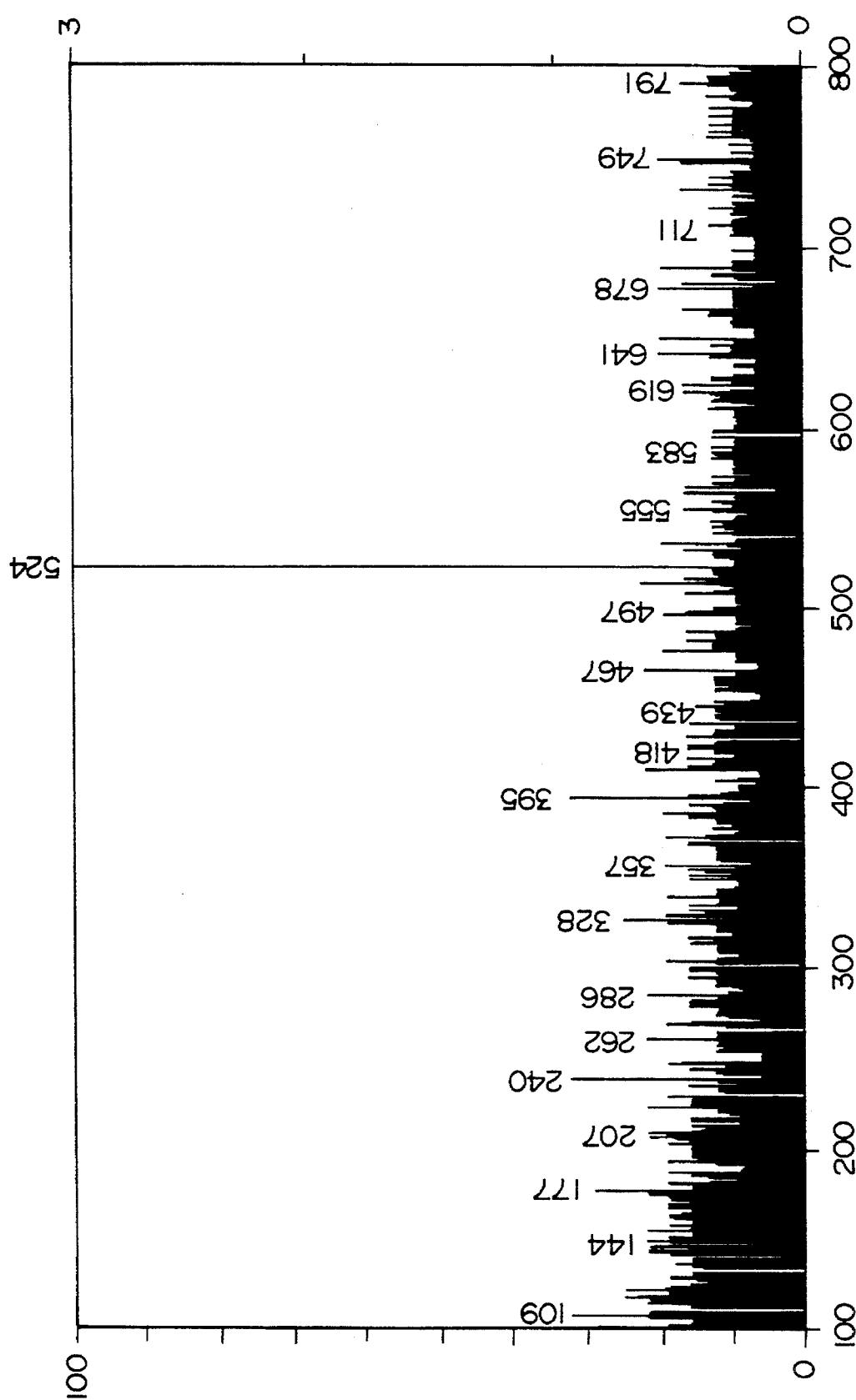
FIG. 3 is a mass spectrum of the product obtained in Synthesis Example 1.

Into a one-liter flask equipped with a stirrer, a thermometer, a thermocouple and a dry air inlet tube were charged 50.00 g (0.233 mole) of 3,3',4,4'-tetraaminobiphenyl, 72.3 mg of 2,5-diphenyl-p-benzoquinone and 700 g of N,N-dimethylformamide under a stream of dry air. After stirring and dissolving the contents of the flask at room temperature, the contents were cooled to −30° C. To the resulting solution was dropwise added a solution prepared by dissolving 72.30 g (0.466 mole) of isocyanatoethyl methacrylate in 50 g of N,N-dimethylformamide over a period of 60 minutes, and the resulting mixture was stirred at that temperature for 6 hours. Then, it was returned to room temperature and the stirring was stopped. The reaction mixture thus obtained was poured into an excessive quantity of water to deposit a white precipitate. The precipitate was collected by filtration and treated with an aqueous solution of acetic acid to separate by-product therefrom, and the main product was washed with water and acetone and recrystallized from methanol to obtain the objective compound. The product thus obtained was identified as 3',4-bis[3-(2-methacryloyloxyethyl)ureido]-3,4'-diaminobiphenyl by referring to IR spectrum, 1H-NMR spectrum, mass spectrum, melting point and elementary analyses as shown below:

(1) IR spectrum (KBr method) shown in FIG. 1
(2) 1H-NMR spectrum (solvent: DMSO-$d_6$) shown in FIG. 2
(3) mass spectrum (FD method) shown in FIG. 3
(4) melting point (measured by DSC): 171.6° C.
(5) elementary analyses:

|  | C (%) | H (%) | N (%) |
| --- | --- | --- | --- |
| Calculated | 59.53 | 6.15 | 16.02 |
| Found | 59.61 | 6.04 | 16.11 |

SYNTHESIS EXAMPLE 2

Figure 4:
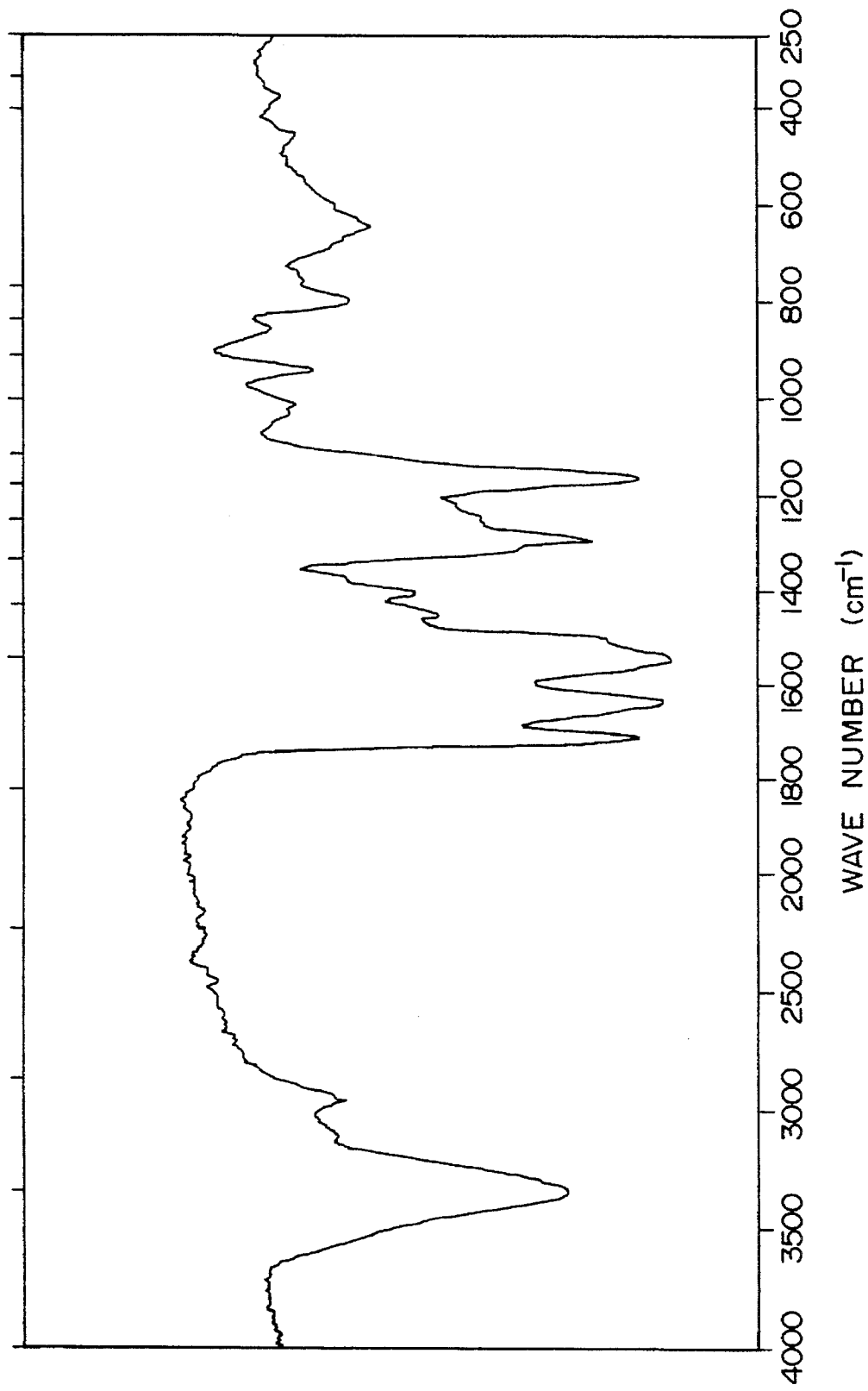
FIG. 4 is an IR spectrum of the product obtained in Synthesis Example 2.
Figure 5:
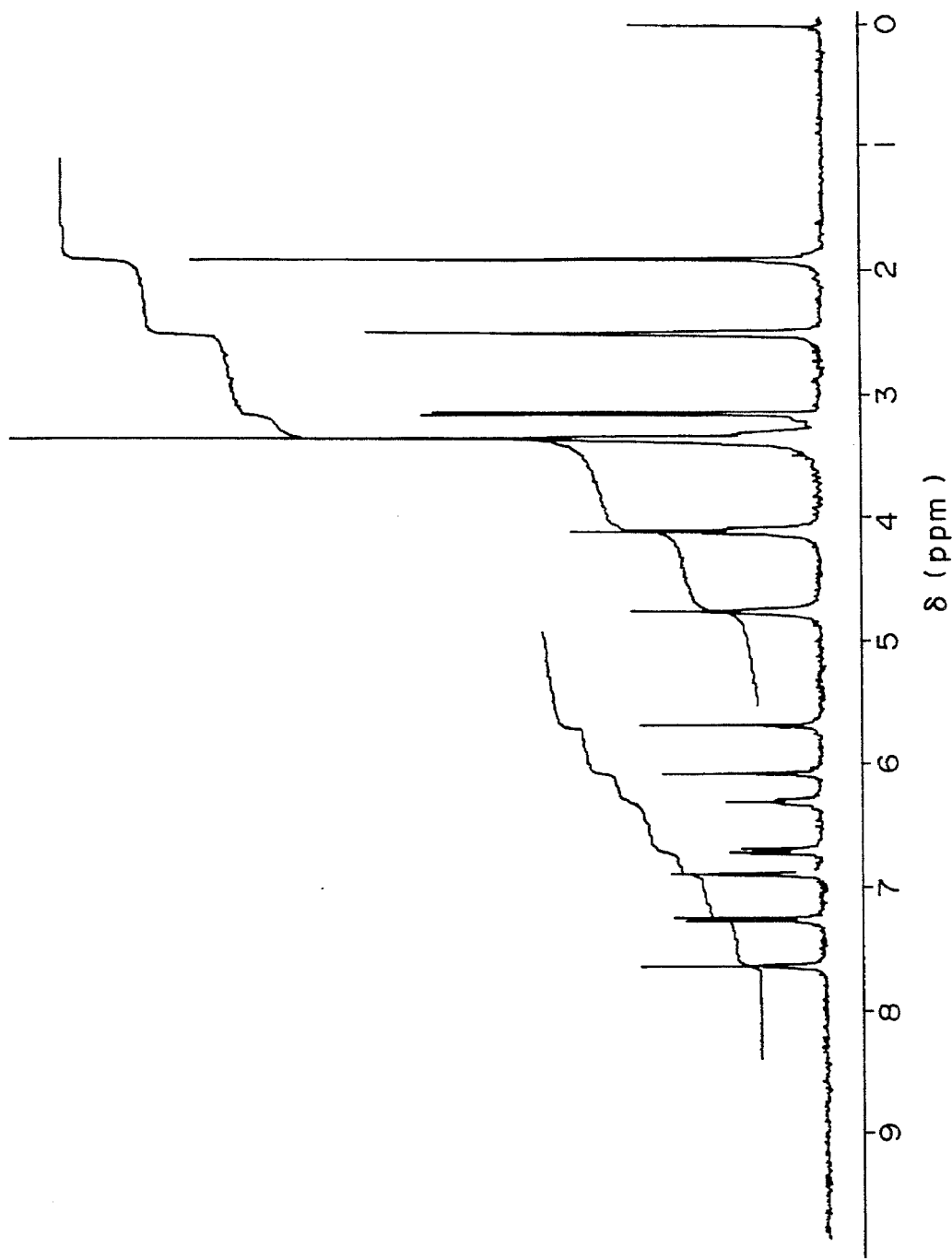
FIG. 5 is a $^1$H-NMR spectrum of the product obtained in Synthesis Example 2.
Figure 6:
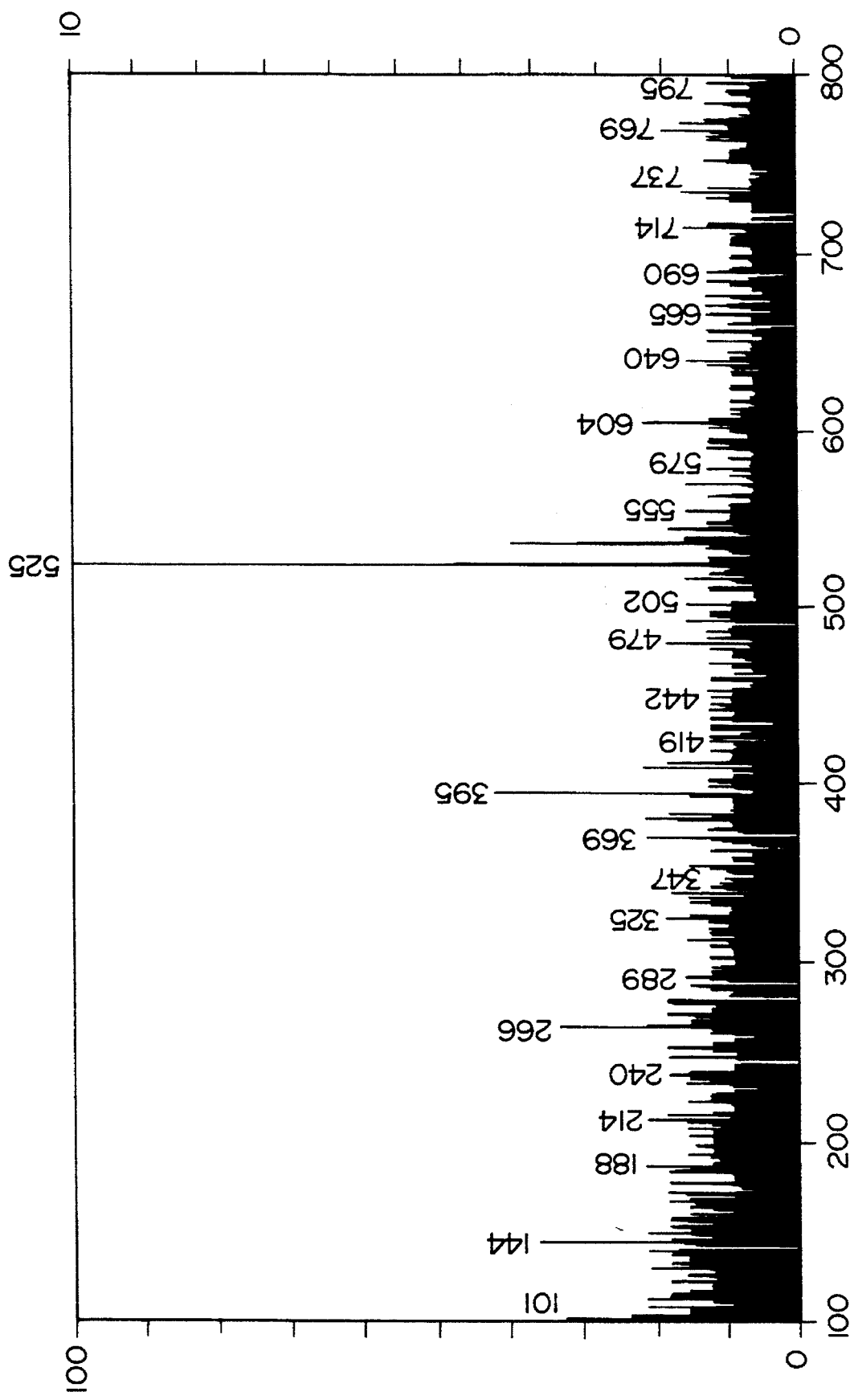
FIG. 6 is a mass spectrum of the product obtained in Synthesis Example 2.

Into a one-liter flask equipped with a stirrer, a thermometer, a thermocouple and a dry air inlet tube were charged 26.313 g (0.0959 mole) of 3,3'-dinitrobenzidine and 270 g of N,N-dimethylacetamide under a stream of dry air. After stirring and dissolving the contents of the flask at room temperature, 72.7 g of di-n-butyltin dilaurate was added and dissolved with stirring at 50° C. The contents of the flask were returned to room temperature, and 59.516 g (0.3836 mole) of isocyanatoethyl methacrylate was added, and the resulting solution was stirred at 50° C. for about 80 hours. After the reaction, the reaction mixture was poured into a large quantity of water to deposit a red viscous substance. The deposited material was washed with water and methanol, and then tetrahydrofuran was added thereto, whereby the objective 4,4'-bis[3-(2-methacryloyloxyethyl)ureido]-3,3'-dinitrobiphenyl was deposited as a yellow powdery material. On the other hand, in a 500 ml flask equipped with a stirrer and a thermometer, 61.2 g of powdery metallic tin was suspended into an aqueous solution of acetic acid [acetic acid/water=61.2 g/30.6 g] to prepare a suspension. To the suspension was added a suspension prepared by suspending 17.89 g (0.0306 mole) of the 4,4'-bis[3-(2-methacryloyloxyethyl)ureido]-3,3'-dinitrobiphenyl obtained above into 185 g of acetic acid, and the resulting mixture was stirred at room temperature for about 10 hours. After the reaction, the reaction mixture was poured into a mixed solution consisting of 300 ml of 28% aqueous ammonia and 3 liters of water to deposit a white precipitate. The precipitate was collected by filtration, and the product was extracted therefrom with dimethylacetamide. The extract was poured into an excessive quantity of water to deposit a white precipitate. After thoroughly washing the precipitate with water, it was recrystallized from a methanol/tetrahydrofuran mixed solvent to obtain 4,4'-bis[3-(2-methacryloyloxyethyl)ureido]-3,3'-diaminobiphenyl. The product thus obtained was identified by referring to IR spectrum, 1H-NMR spectrum, mass spectrum and elementary analyses as shown below:

(1) IR spectrum (KBr method) shown in FIG. 4,
(2) $^1$H-NMR spectrum (solvent: DMSO-$d_6$) shown in FIG. 5,
(3) mass spectrum (FD method) shown in FIG. 6,
(4) elementary analyses:

|  | C (%) | H (%) | N (%) |
| --- | --- | --- | --- |
| Calculated | 59.53 | 6.15 | 16.02 |
| Found | 59.67 | 6.10 | 16.18 |

SYNTHESIS EXAMPLE 3

Into a one-liter flask equipped with a stirrer, a thermometer, a thermocouple and a dry air inlet tube were charged 50.00 g (0.233 mole) of 3,3',4,4'-tetraaminobiphenyl, 72.3 mg of 2,5-diphenyl-p-benzoquinone and 700 g of N-methyl-2-pyrrolidone under a stream of dry air. After stirring and dissolving the contents of the flask at room temperature, the contents were cooled to −15° C. To the solution was dropwise added a solution prepared by dissolving 72.30 g (0.466 mole) of isocyanatoethyl methacrylate in 50 g of N-methyl-2-pyrrolidone over a period of 60 minutes, and the resulting mixture was stirred at that temperature for 6 hours. Then, it was returned to room temperature and the stirring was stopped. The reaction mixture thus obtained was poured into an excessive quantity of water to deposit a white precipitate. The precipitate was collected by filtration and treated with an aqueous solution of acetic acid to separate by-product therefrom, and the main product was washed with water and acetone and recrystallized from methanol to obtain the objective compound.

SYNTHESIS EXAMPLE 4

Into a one-liter flask equipped with a stirrer, a thermometer, a thermocouple and a dry air inlet tube were charged 50.00 g (0.217 mole) of 3,3',4,4'-tetraaminodiphenyl ether, 67.3 mg of 2,5-diphenyl-p-benzoquinone and 700 g of N,N-dimethylformamide under a stream of dry air. After stirring and dissolving the content of the flask at room temperature, it was cooled to −30° C. To the solution was dropwise added a solution prepared by dissolving 67.34 g (0.434 mole) of isocyanatoethyl methacrylate in 50 g of N,N-dimethylformamide over a period of 60 minutes, and the resulting mixture was stirred at that temperature for 6 hours. Then, it was returned to room temperature and the stirring was stopped. The reaction mixture thus obtained was poured into an excessive quantity of water to deposit a white precipitate. The precipitate was collected by filtration and treated with an aqueous solution of acetic acid to separate by-product therefrom, and the main product was washed with water and acetone and recrystallized from methanol to obtain the objective compound.

SYNTHESIS EXAMPLE 5

Into a one-liter flask equipped with a stirrer, a thermometer, a thermocouple and a dry air inlet tube were charged 50.00 g (0.217 mole) of 3,3',4,4'-tetraaminodiphenyl ether, 67.3 mg of 2,5-diphenyl-p-benzoquinone and 700 g of N-methyl-2-pyrrolidone under a stream of dry air. After stirring and dissolving the content of the flask at room temperature, it was cooled to −15° C. To the solution was dropwise added a solution prepared by dissolving 67.34 g (0.434 mole) of isocyanatoethyl methacrylate in 50 g of N-methyl-2-pyrrolidone over a period of 60 minutes, and the resulting mixture was stirred at that temperature for 6 hours. Then, it was returned to room temperature and the stirring was stopped. The reaction mixture thus obtained was poured into an excessive quantity of water to deposit a white precipitate. The precipitate was collected by filtration and treated with an aqueous solution of acetic acid to separate by-product therefrom, and the main product was washed with water and acetone and recrystallized from methanol to obtain the objective compound.

SYNTHESIS EXAMPLE 6

Into a one-liter flask equipped with a stirrer, a thermometer, a thermocouple and a dry air inlet tube were charged 79.736 g (0.152 mole) of 3',4-bis[3-(2-methacryloyloxyethyl)ureido]-3,4'-diaminodiphenyl ether, 45.654 g (0.228 mole) of 4,4'-diaminodiphenyl ether, 0.126 g of 2,5-diphenyl-p-benzoquinone and 756.8 g of N-methyl-2-pyrrolidone. Under a stream of a dry air, the content of the flask was stirred and dissolved at room temperature. To the solution were added 78.259 g (0.266 mole) of 3,3',4,4'-biphenyltetracarboxylic acid dianhydride and 48.624 g (0.114 mole) of 1,3-bis(3,4-dicarboxyphenyl)-1,1,3,3-tetramethyldisiloxane dianhydride, and the resulting mixture was stirred for 5 hours. Thus, a viscous solution of poly(amic acid) resin (hereinafter, referred to as PI-1) was obtained.

SYNTHESIS EXAMPLE 7

Into a one-liter flask equipped with a stirrer, a thermometer, a thermocouple and a dry air inlet tube were charged 64.523 g (0.123 mole) of 4,4'-bis[3-(2-methacryloyloxyethyl)ureido]-3,3'-diaminobiphenyl, 57.468 g (0.287 mole) of 4,4'-diaminodiphenyl ether, 0.125 g of 2,5-diphenyl-p-benzoquinone and 747.5 g of N-methyl-2-pyrrolidone. Under a stream of dry air, the content of the flask was stirred and dissolved at room temperature. To the solution were added 127.185 g (0.410 mole) of 4,4'-oxydiphthalic acid anhydride and the resulting mixture was stirred for 5 hours. Thus, a viscous solution of poly(amic acid) resin (hereinafter, referred to as PI-2) was obtained.

SYNTHESIS EXAMPLE 8

Into a one-liter flask equipped with a stirrer, a thermometer, a thermocouple and a dry air inlet tube were charged 32.524 g (0.062 mole) of 4,4'-bis[3-(2-methacryloyloxyethyl)ureido]-3,3'-diaminobiphenyl, 101.804 g (0.248 mole) of 2,2-bis[4-(4-aminophenoxy)phenyl]-propane, 0.122 g of 2,5-diphenyl-p-benzoquinone and 731.7 g of N-methyl-2-pyrrolidone. Under a stream of dry air, the content of the flask was stirred and dissolved at room temperature. To the solution were added 69.921 g (0.217 mole) of 3,3',4,4'-benzophenonetetracarboxylic acid dianhydride and 39.667 g (0.093 mole) of 1,3-bis(3,4-dicarboxyphenyl)-1,1,3,3-tetramethyldisiloxane dianhydride, and the resulting mixture was stirred for 5 hours. Thus, a viscous solution of poly(amic acid) resin (hereinafter, referred to as PI-3) was obtained.

SYNTHESIS EXAMPLE 9

Into a one-liter flask equipped with a stirrer, a thermometer, a thermocouple and a dry air inlet tube were charged 47.212 g (0.09 mole) of 3',4-bis[3-(2-methacryloyloxyethyl)ureido]-3,4'-diaminobiphenyl, 70.196 g (0.21 mole) of 1,1,1,3,3,3-hexafluoro-2,2-bis(4-aminophenyl)-propane, 0.125 g of 2,5-diphenyl-p-benzoquinone and 748.8 g of N-methyl-2-pyrrolidone. Under a stream of dry air, the content of the flask was stirred and dissolved at room temperature. To the solution were added 106.617 g (0.24 mole) of 1,1,1,3,3,3-hexafluoro-2,2-bis(3,4-dicarboxyphenyl)propane dianhydride and 25.591 g (0.06 mole) of 1,3-bis(3,4-dicarboxyphenyl)-1,1,3,3-tetramethyldisiloxane dianhydride, and the resulting mixture was stirred for 5 hours. Thus, a viscous solution of poly(amic acid) resin (hereinafter, referred to as PI-4) was obtained.

SYNTHESIS EXAMPLE 10

Into a one-liter flask equipped with a stirrer, a thermometer, a thermocouple and a dry air inlet tube were charged 68.113 g (0.126 mole) of 3',4-bis[3-(2-methacryloyloxyethyl)ureido]-3,4'-diaminodiphenyl ether, 58.869 g (0.294 mole) of 4,4'-diaminodiphenyl ether, 0.122 g of 2,5-diphenyl-p-benzoquinone and 734.6 g of N-methyl-2-pyrrolidone. Under a stream of dry air, the content of the flask was stirred and dissolved at room temperature. To the solution were added 64.126 g (0.294 mole) of pyromellitic dianhydride and 53.742 g (0.126 mole) of 1,3-bis(3,4-dicarboxyphenyl)-1,1,3,3-tetramethyldisiloxane dianhydride, and the resulting mixture was stirred for 5 hours. Thus, a viscous solution of poly(amic acid) resin (hereinafter, referred to as PI-5) was obtained.

SYNTHESIS EXAMPLE 11

Into a one-liter flask equipped with a stirrer, a thermometer, a thermocouple and a dry air inlet tube were charged 45.408 g (0.084 mole) of 3',4-bis[3-(2-methacryloyloxyethyl)ureido]-3,4'-diaminodiphenyl ether, 101.616 g (0.196 mole) of 1,1,1,3,3,3-hexafluoro-2,2-bis[4-(4-aminophenoxy)phenyl]-propane, 0.125 g of 2,5-diphenyl-p-benzoquinone and 750.5 g of N-methyl-2-pyrrolidone. Under a stream of dry air, the content of the flask was stirred and dissolved at room temperature. To the solution were added 43.429 g (0.140 mole) of 4,4'-oxydiphthalic acid anhydride and 59.713 g (0.140 mole) of 1,3-bis(3,4-dicarboxyphenyl)-1,1, 3,3-tetramethyldisiloxane dianhydride, and the resulting mixture was stirred for 5 hours. Thus, a viscous solution of poly(amic acid) resin (hereinafter, referred to as PI-6) was obtained.

SYNTHESIS EXAMPLE 12

Into a one-liter flask equipped with a stirrer, a thermometer, a thermocouple and a dry air inlet tube were charged 21.4 g (0.1 mole) of 3,3'4,4-tetraaminobiphenyl, 20.0 g (0.1 mole) of 4,4'-diaminodiphenyl ether and 100 g of N-methyl-2-pyrrolidone. Under a stream of dry air, the content of the flask was stirred and dissolved at room temperature, and then cooled to 0°–3° C. To the solution was added a solution prepared by dissolving 48.3 g (0 15 mole) of 3,3',4,4'-benzophenonetetracarboxylic acid dianhydride and 21.3 g (0.05 mole) of 1,3-bis(3,4-dicarboxyphenyl)-1,1,3,3-tetramethyldisiloxane dianhydride in 250 g of N-methyl-2-pyrrolidone over a period of 2 hours, and the resulting mixture was stirred at that temperature for 5 hours. Then, 31 mg of 2,5-diphenyl-p-benzoquinone was dissolved in the solution thus obtained, and 31.0 g (0.2 mole) of isocyanatoethyl methacrylate was dropwise added at that temperature over a period of 20 minutes, and the resulting mixture was stirred for 2 hours. Thus, a viscous solution of poly(amic acid) resin was obtained. This poly(amic acid) solution was named PI-7.

SYNTHESIS EXAMPLE 13

Into a one liter flask equipped with a stirrer, a thermometer, a thermocouple and a dry air inlet tube were charged 20.0 g (0.1 mole) of 4,4'-diaminodiphenyl ether and 230 g of N-methyl-2-pyrrolidone. Under a stream of dry air, the content of the flask was stirred and dissolved at room temperature, and then cooled to 0°–3° C. To the solution were added 48.3 g (0.15 mole) of 3,3',4,4'-benzophenonetetracarboxylic acid dianhydride and 21.3 g (0.05 mole) of 1,3-bis(3,4-dicarboxyphenyl)-1,1,3,3-tetramethyldisiloxane dianhydride and stirred and dissolved at that temperature. Then, a solution prepared by dissolving 21.4 g (0.1 mole) of 3,3',4,4'-tetraaminobiphenyl in 26 g of N-methyl-2-pyrrolidone was added and stirred at that temperature for 5 hours. Then, 31 mg of 2,5-diphenyl-p-benzoquinone was dissolved in the solution thus obtained, and 31.0 g (0.2 mole) of isocyanatoethyl methacrylate was dropwise added over a period of 20 minutes, and the resulting mixture was stirred for 2 hours. Thus, a viscous solution of poly(amic acid) resin was obtained. This poly(amic acid) solution was named PI-8.

SYNTHESIS EXAMPLE 14

Into a one-liter flask equipped with a stirrer, a thermometer, a thermocouple and a dry air inlet tube were charged 32.1 g (0.15 mole) of 3,3',4,4'-tetraaminobiphenyl, 47 mg of 2,5-diphenyl-p-benzoquinone and 270 g of N-methyl-2-pyrrolidone. The content of the flask was stirred and dissolved at room temperature, and then cooled to −15° C. To the solution was dropwise added 46.5 g (0.3 mole) of isocyanatoethyl methacrylate over a period of 60 minutes, and the resulting mixture was stirred at that temperature for 4 hours. Then, the temperature was elevated to 0°–3° C., and 10.0 g (0.05 mole) of 4,4'-diaminodiphenyl ether was added, and stirred and dissolved. Further, to the resulting solution were added 32.2 g (0.1 mole) of 3,3',4,4'-benzophenonetetracarboxylic acid dianhydride, 22.2 g (0.05 mole) of 2,2-bis(3,4-dicarboxyphenyl)-hexafluoropropane dianhydride and 21.3 g (0.05 mole) of 1,3bis-(3,4-dicarboxyphenyl)-1,1,3,3-tetramethyldisiloxane dianhydride, and the resulting mixture was stirred at that temperature for 5 hours. Thus, a viscous solution of poly(amic acid) resin was obtained. This poly(amic acid) solution was named PI-9.

SYNTHESIS EXAMPLE 15

Into a one-liter flask equipped with a stirrer, a thermometer, a thermocouple and a dry air inlet tube were charged 32.1 g (0.15 mole) of 3,3',4,4'-tetraaminobiphenyl, 47 mg of 2,5-diphenyl-p-benzoquinone and 300 g of N,N-dimethylformamide. The content of the flask was stirred and dissolved at room temperature, and then cooled to −30° C. To the solution was dropwise added 46.5 g (0.3 mole) of isocyanatoethyl methacrylate over a period of 60 minutes, and the resulting mixture was stirred at that temperature for 6 hours. Then, the temperature was elevated to 0°–3° C., and 10.0 g (0.05 mole) of 4,4'-diaminodiphenyl ether was added, and stirred and dissolved. Further, to the resulting solution were added 32.2 g (0.1 mole) of 3,3',4,4'-benzophenonetetracarboxylic acid dianhydride, 22.2 g (0.05 mole) of 2,2-bis(3,4-dicarboxyphenyl)-hexafluoropropane dianhydride and 21.3 g (0.05 mole) of 1,3-bis(3,4-dicarboxyphenyl)-1, 1,3,3-tetramethyldisiloxane dianhydride, and the resulting mixture was stirred at that temperature for 5 hours. Then the temperature was elevated to 70° C. and the mixture was heated at that temperature for 8 hours. Thus, a viscous solution of poly(amic acid) resin was obtained. This poly(amic acid) solution was named PI-10.

SYNTHESIS EXAMPLE 16

Into a one-liter flask equipped with a stirrer, a thermometer, a thermocouple and a dry air inlet tube were charged 24.2 g (0.075 mole) of 3,3',4,4'-benzophenonetetracarboxylic acid dianhydride, 10.7 g (0.025 mole) of 1,3-bis(3,4-dicarboxyphenyl)-1,1,3,3-tetramethyldisiloxane dianhydride, 200 ml of N-methyl-2-pyrrolidone and 26.0 g (0.2 mole) of 2-hydroxyethyl methacrylate. The content of the flask was heated to 80° C. and stirred for 4 hours. While cooling the solution thus obtained with ice, 35 g of thionyl chloride was dropwise added thereto over a period of one hour, and the resulting mixture was stirred at room temperature for 2 hours. Then, 20.0 g (0.1 mole) of 4,4'-diaminodiphenyl ether was added thereto, and the resulting mixture was stirred for 8 hours. Then, 40 ml of ethanol was added and stirred for 4 hours, and the resulting mixture was slowly poured into 5 liters of water to deposit a stringy solid product. It was dissolved in N-methyl-2-pyrrolidone to obtain a viscous solution of poly(amic acid) resin. This poly(amic acid) solution was named PI-11.

SYNTHESIS EXAMPLE 17

Into a one-liter flask equipped with a stirrer, a thermometer, a thermocouple and a dry air inlet tube were charged 34.541 g (0.15 mole) of 3,3',4,4'-tetraaminodiphenyl ether, 82 mg of 2,5-diphenyl-p-benzoquinone and 400 g of N,N-dimethylformamide. The content of the flask was stirred and dissolved at room temperature, and cooled to −30° C. To the solution thus obtained was dropwise added a solution prepared by dissolving 46.546 g (0.3 mole) of isocyanatoethyl methacrylate in 100 g of N,N-dimethylformamide over a period of 60 minutes, and the resulting mixture was stirred at that temperature for 6 hours. Then, the temperature was elevated to 0°–3° C., and 10.012 g (0.05 mole) of 4,4'-diaminodiphenyl ether was added thereto, and the resulting mixture was stirred and dissolved. Then, 32.222 g (0.1 mole) of 3,3',4,4'-benzophenonetetracarboxylic acid dianhydride, 22.212 g (0.05 mole) of 2,2-bis(3,4-dicarboxyphenyl)-hexafluoropropane dianhydride and 21.326 g (0.05 mole) of 1,3-bis(3,4-dicarboxyphenyl)-1,1,3,3-tetramethyldisiloxane dianhydride were added, and the resulting mixture was stirred at that temperature for 5 hours. Thus, a viscous solution of poly(amic acid) resin (hereinafter, referred to as PI-12) was obtained.

SYNTHESIS EXAMPLE 18

Into a one-liter flask equipped with a stirrer and a refluxing device were charged 150 g (0.51 mole) of 3,3',4,4'-biphenyltetracarboxylic acid dianhydride and 380 g of dry methanol. After carrying out a reaction for 11 hours under reflux, the excessive methanol was completely distilled off from the solution and the residue was dried to obtain dimethyl 3,3',4,4'-biphenyltetracarboxylate.

Next, 107.488 g (0.300 mole) of the dimethyl 3,3',4,4'-biphenyltetracarboxylate thus obtained was dissolved in 150 ml of N,N-dimethylacetamide in a one liter flask equipped with a stirrer, a thermometer, a thermocouple and a dry air inlet tube, and 123.796 g (0.6 mole) of dicyclohexylcarbodiimide dissolved in 150 ml of N,N-dimethylacetamide was dropped thereinto while cooling the system with ice. Further, a solution of 61.900 g (0.118 mole) of 3',4-bis[3-(2-methacryloyloxyethyl)ureido]-3,4'-diaminobiphenyl, 35.242 g (0,176 mole) of 4,4'-diaminodiphenyl ether and 0.102 g of 2,5-diphenyl-p-benzoquinone in 150 ml of N,N-dimethylacetamide was dropped thereinto, and the resulting mixture was stirred at room temperature for 15 hours. Then, 12 g of ethanol was added to the solution, and the deposited matter was filtered off. The filtrate was poured into a large quantity of water to deposit a solid product. After dryness, it was dissolved in N-methyl-2-pyrrolidone to obtain a solution of poly(amic acid) ester resin (hereinafter referred to as PI-13).

SYNTHESIS EXAMPLE 19

Into a one-liter flask equipped with a stirrer and a refluxing device were charged 150 g (0.484 mole) of 4,4'-oxydiphthalic acid anhydride and 360 g of dry methanol. After carrying out a reaction for 11 hours under reflux, the excessive methanol was completely distilled off from the solution and the residue was dried to obtain monomethyl 4,4'-oxydiphthalate.

Next, 112.288 g (0.3 mole) of the monomethyl 4,4'-oxydiphthalate thus obtained was dissolved in 150 ml of N,N-dimethylacetamide in a one liter flask equipped with a stirrer, a thermometer, a thermocouple and a dry air inlet tube, and 123.796 g (0.6 mole) of dicyclohexylcarbodiimide dissolved in 150 ml of N,N-dimethylacetamide was dropped thereinto while cooling the system with ice. Further, a solution of 61.900 g (0.118 mole) of 3',4-bis[3-(2-methacryloyloxyethyl)ureido]-3,4'-diaminobiphenyl, 35.242 g (0.176 mole) of 4,4'-diaminodiphenyl ether and 0.105 g of 2,5-diphenyl-p-benzoquinone in 150 ml of N,N-dimethylacetamide was dropped thereinto, and the resulting mixture was stirred at room temperature for 15 hours. Then, 12 g of ethanol was added to the solution, and the deposited matter was filtered off. The filtrate was poured into a large quantity of water to deposit a solid product. After dryness, it was dissolved into N-methyl-2-pyrrolidone to obtain a solution of poly(amic acid) ester resin (hereinafter referred to as PI-14).

SYNTHESIS EXAMPLE 20

Into a one-liter flask equipped with a stirrer and a refluxing device were charged 150 g (0.51 mole) of 3,3',4,4'-biphenyltetracarboxylic acid dianhydride and 380 g of dry methanol. After carrying out a reaction for 11 hours under reflux, the excessive methanol was completely distilled off from the solution and the residue was dried to obtain dimethyl 3,3',4,4'-biphenyltetracarboxylate.

Next, 107.488 g (0.300 mole) of the dimethyl 3,3',4,4'-biphenyltetracarboxylate thus obtained was dissolved in 150 ml of N,N-dimethylacetamide in a one liter flask equipped with a stirrer, a thermometer, a thermocouple and a dry air inlet tube, and 123.796 g (0.6 mole) of dicyclohexylcarbodiimide dissolved in 150 ml of N,N-dimethylacetamide was dropped thereinto while cooling the system with ice. Further, a solution of 61.900 g (0.118 mole) of 4,4'-bis[3-(2-methacryloyloxyethyl)ureido]-3,3'-diaminobiphenyl, 35.242 g (0.176 mole) of 4,4'-diaminodiphenyl ether and 0.102 g of 2,5-diphenyl-p-benzoquinone in 150 ml of N,N-dimethylacetamide was dropped thereinto, and the resulting mixture was stirred at room temperature for 15 hours. Then, 12 g of ethanol was added to the solution, and the deposited matter was filtered off. The filtrate was poured into a large quantity of water to deposit a solid product. After dryness, it was dissolved in N-methyl-2-pyrrolidone to obtain a solution of poly(amic acid) ester resin (hereinafter referred to as PI-15).

SYNTHESIS EXAMPLE 21

Into a one-liter flask equipped with a stirrer and a refluxing device were charged 150 g (0.484 mole) of 4,4'-oxydiphthalic acid anhydride and 360 g of dry methanol. After carrying out a reaction for 11 hours under reflux, the excessive methanol was completely distilled off from the solution and the residue was dried to obtain monomethyl 4,4'-oxydiphthalate.

Next, 112.288 g (0.3 mole) of the monomethyl 4,4'-oxydiphthalate thus obtained was dissolved in 150 ml of N,N-dimethylacetamide in a one liter flask equipped with a stirrer, a thermometer, a thermocouple and a dry air inlet tube, and 123.796 g (0.6 mole) of dicyclohexylcarbodiimide dissolved in 150 ml of N,N-dimethylacetamide was dropped thereinto while cooling the system with ice. Further, a solution of 61.900 g (0.118 mole) of 4,4'-bis[3-(2-methacryloyloxyethyl)ureido]-3,3'-diaminobiphenyl, 35.242 g (0.176 mole) of 4,4'-diaminodiphenyl ether and 0.105 g of 2,5-diphenyl-p-benzoquinone in 150 ml of N,N-dimethylacetamide was dropped thereinto, and the resulting mixture was stirred at room temperature for 15 hours. Then, 12 g of ethanol was added to the solution, and the deposited matter was filtered off. The filtrate was poured into a large quantity of water to deposit a solid product. After dryness, it was dissolved in N-methyl-2-pyrrolidone to obtain a solution of poly(amic acid) ester resin (hereinafter referred to as PI-16).

SYNTHESIS EXAMPLE 22

In a one-liter flask equipped with a stirrer, a thermometer, a thermocouple and a dry air inlet tube, 88.262 g (0.3 mole) of 3,3',4,4'-biphenyltetracarboxylic acid dianhydride, 150 ml of N,N-dimethylacetamide, 78.084 g (0.6 mole) of 2-hydroxyethyl methacrylate and 47.46 g (0.6 mole) of pyridine were stirred at room temperature for 48 hours under a stream of dry air. While cooling the system with ice, a solution of 123.796 g (0.6 mole) of dicyclohexylcarbodiimide in 150 ml of N,N-dimethylacetamide was dropped into the solution, and further a solution of 58.869 g (0.294 mole) of 4,4'-diaminodiphenyl in 150 ml of N,N-dimethylacetamide was dropped thereinto, and the resulting mixture was stirred at room temperature for 17 hours. Then, 12 g of ethanol was added to the solution and the deposited matter was filtered off. The filtrate was poured into a large quantity of water to deposit a solid product. It was dissolved in N-methyl-2-pyrrolidone to obtain a solution of poly(amic acid) ester resin (hereinafter referred to as PI-17).

EXAMPLES 1–15

Each 10 grams portion of the poly(amic acid) resin solutions and poly(amic acid) ester resin solutions obtained in the above-mentioned Synthesis Examples, i.e. PI-1 to PI-10 and PI-12 to PI-16, was compounded with the materials shown in Table 1 and stirred and mixed to prepare the photosensitive resin compositions to be tested in Examples 1–15. Next, each of these solutions was filtered through a filter, dropped onto a silicon wafer and spin-coated so as to give a final cured film thickness of 10 μm, provided that in Examples 7–10 the spin-coating was carried out so as to give a final cured film thickness of 5 μm. Then, the coated film was heated on a hot plate at 100° C. for 100–200 seconds, the coating surface was pattern-masked, and then it was exposed to ultrahigh pressure mercury lamp (3 mW/cm$^2$ i ray), provided that the exposure was as shown in Table 2. After dip-developing it with a prescribed developer shown in Table 2, it was rinsed with deionized water or a solvent (methanol, toluene or the like). Then by heating it first at 100° C. for 15 minutes, then at 200° C. for 60 minutes and finally at 350° C. for 60 minutes in an atmosphere of nitrogen, a ring-closure reaction took place to form polyimidazopyrrolone or polyimidazopyrrolonimide. In all the cases, through holes of 10 μm could be formed.

Further, each of the samples PI-1 to PI-10 and PI-12 to PI-16 was coated onto a glass substrate and heated first at 100° C. for 15 minutes, then at 200° C. for 60 minutes and finally at 350° C. for 60 minutes in an atmosphere of nitrogen. On the film thus formed having a film thickness of 25 μm, tensile strength was measured by the use of a tensile tester (Tensilon All-purpose Testing Machine Model UCT-5T, manufactured by Orientic Co.) to reveal that all the samples were excellent in film strength. The results of evaluation of image-formability and film strength are summarized in Table 2.

COMPARATIVE EXAMPLES 1 AND 2

The procedure of Examples 1–15 was repeated, except that the poly(amic acid) ester resin solutions PI-11 and PI-17 obtained in Synthesis Examples 16 and 22 were used, provided that in Comparative Example 1 the spin-coating was carried out so as to give a final film thickness of 5 μm. Although good relief patterns could be obtained in these experiments, the films were inferior in strength. The results of evaluation are shown in Table 2.

TABLE 1

|  | Poly(amic acid) resin solution | Polymerizable unsaturated compound | Photo-initiator |
|---|---|---|---|
| Example 1 | PI-1 (10 g) | — | C-2/BTTB (0.01 g/0.4 g) |
| Example 2 | PI-2 (10 g) | A-4G (1.0 g) | NK-1342/BTTB (0.1 g/0.4 g) |
| Example 3 | PI-3 (10 g) | A-4G (1.0 g) | C-1/BTTB (0.05 g/0.2 g) |
| Example 4 | PI-4 (10 g) | — | NK-1342/BTTB (0.03 g/0.4 g) |
| Example 5 | PI-5 (10 g) | — | NK-1342/BTTB (0.02 g/0.4 g) |
| Example 6 | PI-6 (10 g) | A-4G (1.0 g) | C-2/BTTB (0.05 g/0.4 g) |
| Example 7 | PI-7 (10 g) | — | K-1/NPG (0.02 g/0.1 g) |
| Example 8 | PI-8 (10 g) | A-4G (1.4 g) | K-1/NPG (0.02 g/0.1 g) |
| Example 9 | PI-9 (10 g) | IMU (1.4 g) | K-2/NPG (0.02 g/0.1 g) |
| Example 10 | PI-10 (10 g) | — | K-2/NPG (0.03 g/0.2 g) |
| Example 11 | PI-12 (10 g) | — | C-2/BTTB (0.03 g/0.2 g) |
| Example 12 | PI-13 (10 g) | — | C-1/BTTB (0.05 g/0.4 g) |
| Example 13 | PI-14 (10 g) | A-4G (1.0 g) | C-2/BTTB (0.05 g/0.4 g) |
| Example 14 | PI-15 (10 g) | A-4G (1.0 g) | NK-1342/BTTB (0.03 g/0.4 g) |
| Example 15 | PI-16 (10 g) | — | C-2/BTTB (0.05 g/0.4 g) |
| Comparative Example 1 | PI-11 (10 g) | IMU/A-4G (0.6 g/0.8 g) | K-2/NPG (0.02 g/0.1 g) |
| Comparative Example 2 | PI-17 (10 g) | IMU/A-4G (0.6 g/0.8 g) | C-2/BTTB (0.02 g/0.1 g) |

TABLE 2

|  | Exposure (mJ/cm$^2$) | Developer | Image-formability | Film strength |
|---|---|---|---|---|
| Example 1 | 200 | TMAH aq. | Good | Good |
| Example 2 | 200 | TMAH aq. | Good | Good |
| Example 3 | 200 | TMAH aq. | Good | Good |
| Example 4 | 200 | TEA aq. | Good | Good |
| Example 5 | 200 | TEA aq. | Good | Good |
| Example 6 | 200 | TMAH aq. | Good | Good |
| Example 7 | 600 | TEA aq. | Good | Good |
| Example 8 | 600 | TEA aq. | Good | Good |
| Example 9 | 600 | MEA aq. | Good | Good |
| Example 10 | 600 | MEA aq. | Good | Good |
| Example 11 | 200 | MEA aq. | Good | Good |
| Example 12 | 200 | NMP/TLS (8 g/2 g) | Good | Good |
| Example 13 | 200 | NMP/TLS (8 g/2 g) | Good | Good |
| Example 14 | 200 | NMP/TLS (8 g/2 g) | Good | Good |
| Example 15 | 200 | NMP/TLS (8 g/2 g) | Good | Good |

5,472,823

TABLE 2-continued

| | Exposure (mJ/cm$^2$) | Developer | Image-formability | Film strength |
|---|---|---|---|---|
| Comparative Example 1 | 600 | TEA aq. | Good | Not good |
| Comparative Example 2 | 200 | NMP/TLS (8 g/2 g) | Good | Good |

In Tables 1 and 2, the meanings of the symbols are as follows:

IMU:

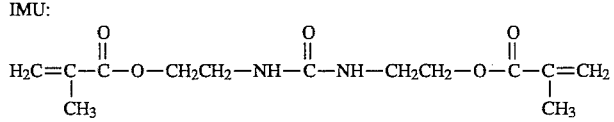

A-4G: tetraethylene glycol diacrylate, manufactured by Shin-Nakamura Kagaku Co.
C-1: 7-diethylamino-4-methylcoumarin
C-2: 4,6-dimethyl-7-ethylaminocoumarin

NK-1342:

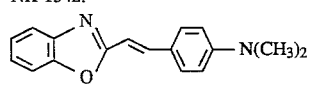

BTTB:

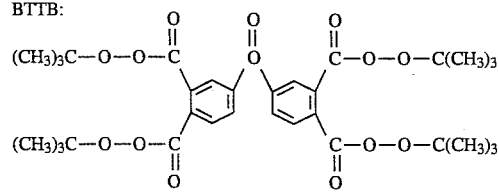

K-1: 2,6-bis(p-diethylaminobenzylidene)-4-methyl-4-azacyclohexanone
K-2: 3,3'-carbonylbis(7-diethylamino)-coumarin
NPG: N-(4-cyanophenyl)-glycine
TMAH: tetramethylammonium hydroxide
MEA: monoethanolamine
TEA: triethanolamine
NMP: N-methyl-2-pyrrolidone
TLS: toluene.

The diamino compound of the formula (I) of this invention is useful as a constituent monomer of poly(amic acid) resin, poly(amic acid) ester resin and/or polyimide resin which are excellent photosensitive resins. The photosensitive resin composition of this invention exhibits an excellent developability and is excellent in workability and cost. Cured films of polyimidazopyrrolone resin and polyimidazopyrroloneimide resin prepared from the photosensitive resin composition of this invention are comparable to prior art non-photosensitive polyimides in film strength, heat resistance and adhesiveness, and they are low in thermal expansion due to the formation of imidazopyrrolone rings, and therefore are excellent in film characteristics. Further, they are free from chloride pollution and superior in film strength as compared with the co-valent bond type photosensitive polyimides prepared by introducing photosensitive groups into a poly(amic acid) through intermediation of ester bonds.

What is claimed is:

1. A photosensitive resin composition comprising:

(A) a poly(amic acid) resin having recurring units represented by the formula:

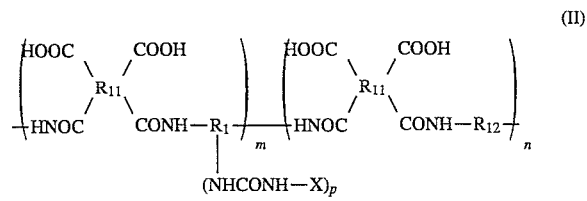

wherein X is a monovalent photosensitive group; $R_1$ is a (2+p)-valent organic group; $R_{11}$ is a tetravalent organic group; $R_{12}$ is a divalent organic group; p is an integer of 1 to 12; and m and n are molar numbers of recurring units, and m/n is 1/99 to 100/0 and/or a poly(amic acid) ester resin obtained by esterifying the carboxyl group of said poly(amic acid) resin and/or a polyimide resin obtained by a dehydrating or alcohol-eliminating ring-closure reaction of said poly(amic acid) resin or poly(amic acid) ester resin; and (B) an optionally used photo-initiator.

2. A photosensitive resin composition according to claim 1, wherein said ingredient (A) is a poly(amic acid) resin wherein X in the formula (II) is one of the groups represented by the formulae:

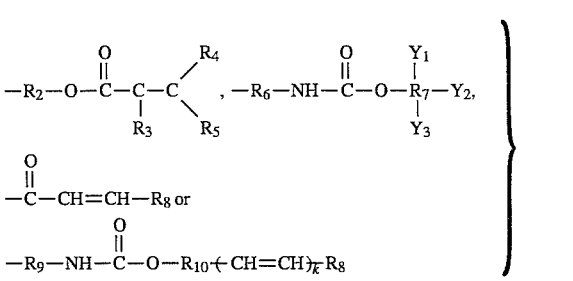

wherein $R_2$ is a divalent group obtained from an alkyl group containing 1 to 18 carbon atoms; $R_6$ and $R_9$ are independently a divalent group obtained from an alkyl group containing 6 to 9 carbon atoms, a divalent group obtained from a cycloalkyl group containing 6 to 13 carbon atoms which may contain a methyl or methoxy group, or a divalent aromatic group which may have a methyl or methoxy group;

$R_{10}$ is a divalent organic group; $R_3$, $R_4$ and $R_5$ are independently a hydrogen atom or an alkyl group containing 1 to 3 carbon atoms; $R_7$ is a tetravalent organic group; $R_8$ is a monovalent aromatic or heterocyclic group; $Y_1$, $Y_2$ and $Y_3$ are independently a hydrogen atom or a monovalent organic group having a vinyl group, provided that at least one of $Y_1$, $Y_2$ and $Y_3$ is a monovalent organic group having a vinyl group; and k is 1 or 2; and/or a poly(amic acid) ester resin obtained by esterifying the carboxyl group of said poly(amic acid) resin and/or a polyimide resin obtained by dehydrating or alcohol-eliminating ring-closure reaction of said poly(amic acid) resin or poly(amic acid) ester resin.

3. A composition according to claim 1, which comprises
   (A) a poly(amic acid) ester resin obtained by esterifying the carboxyl group of said poly(amic acid) resin, and
   (B) a photo-initiator.

4. A composition according to claim 3, wherein the poly(amic acid) ester resin is represented by the formula:

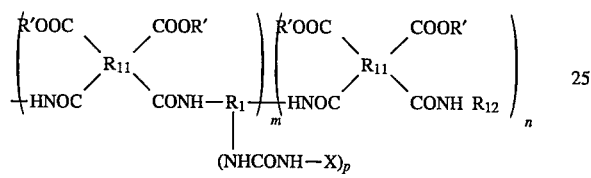

wherein $R_{11}$ is

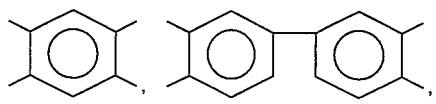

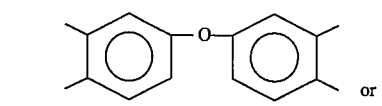

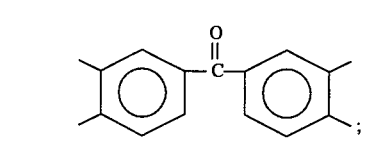

$R_1$ is

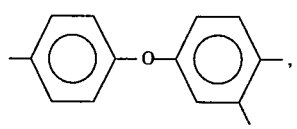

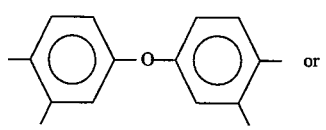

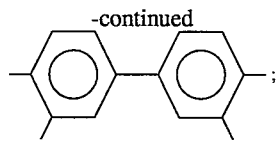

$R_{12}$ is

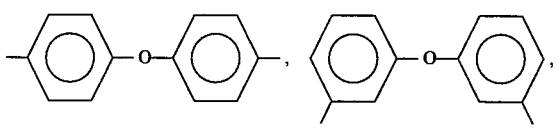

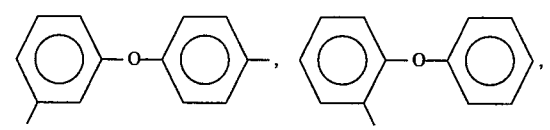

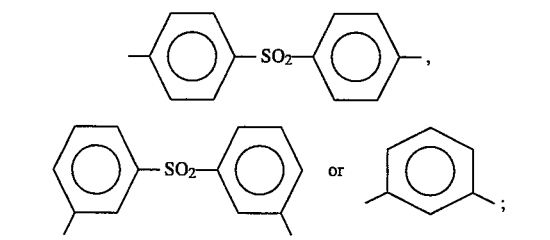

X is

P is 1 or 2;

m/n is 30–100/70–0;

R' is —CH$_3$, —C$_2$H$_5$, —C(CH$_3$)$_3$, —Si(CH$_3$)$_3$, —Si(C$_2$H$_5$)$_3$, or —Si(t-Bu)(CH$_3$)$_2$.

5. A composition which comprises
   (A) a poly(amic acid) ester resin of the formula:

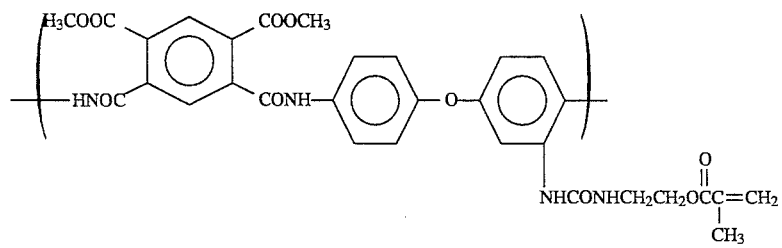
and
(B) as a photo-initiator, a mixture of 4,6-dimethyl-7-ethylaminocoumarin, and
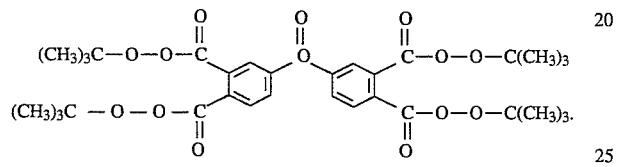
* * * * *